(12) United States Patent
Biggadike et al.

(10) Patent No.: US 7,579,335 B2
(45) Date of Patent: *Aug. 25, 2009

(54) ANDROSTANE 17α-CARBONATE DERIVATIVES FOR USE IN THE TREATMENT OF ALLERGIC AND INFLAMMATORY CONDITIONS

(75) Inventors: Keith Biggadike, Stevenage (GB); Deborah Needham, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 85 days.

This patent is subject to a terminal disclaimer.

(21) Appl. No.: 11/813,227

(22) PCT Filed: Jan. 9, 2006

(86) PCT No.: PCT/EP2006/000149

§ 371 (c)(1),
(2), (4) Date: Jul. 2, 2007

(87) PCT Pub. No.: WO2006/072599

PCT Pub. Date: Jul. 13, 2006

(65) Prior Publication Data

US 2008/0182831 A1    Jul. 31, 2008

(30) Foreign Application Priority Data

Jan. 10, 2005  (GB)  ................................. 0500405.6
Sep. 14, 2005  (GB)  ................................. 0518774.5

(51) Int. Cl.
A61K 31/56    (2006.01)
C07J 3/00    (2006.01)

(52) U.S. Cl. .................... 514/179; 514/180; 552/610

(58) Field of Classification Search ................ 552/610; 514/179, 180

See application file for complete search history.

(56) References Cited

U.S. PATENT DOCUMENTS

| 3,856,828 | A |   | 12/1974 | Phillipps et al. |
| 4,996,335 | A | * | 2/1991 | Bodor ........................ 552/610 |
| 5,552,438 | A |   | 9/1996 | Christensen, IV |
| 6,172,054 | B1 |  | 1/2001 | Clark |
| 6,245,804 | B1 |  | 6/2001 | Lehmann et al. |
| 6,395,738 | B1 |  | 5/2002 | Ohshima et al. |
| 6,897,224 | B2 |  | 5/2005 | Jaroch et al. |
| 7,288,536 | B2 |  | 10/2007 | Biggadike et al. |
| 7,291,609 | B2 |  | 11/2007 | Biggadike et al. |

FOREIGN PATENT DOCUMENTS

| GB | 1384372 A | 2/1975 |
| GB | 1514476 A | 6/1978 |
| GB | 2079755 A | 1/1982 |
| GB | 2137206 A | 10/1984 |
| WO | 8903390 A1 | 4/1989 |
| WO | 9313055 A1 | 7/1993 |
| WO | 9534534 A1 | 12/1995 |
| WO | 9741867 A1 | 11/1997 |
| WO | 9830537 A1 | 7/1998 |
| WO | 9854159 A1 | 12/1998 |
| WO | 9916766 A1 | 4/1999 |
| WO | 9932127 A1 | 7/1999 |
| WO | 9947505 A1 | 9/1999 |
| WO | 9962875 A1 | 12/1999 |
| WO | 0066590 A2 | 11/2000 |
| WO | 0104118 A2 | 1/2001 |
| WO | 0110143 A1 | 2/2001 |

(Continued)

OTHER PUBLICATIONS

Ray et al.; "Induction of the E-selectin promoter by interleukin 1 and tumor necrosis factor alpha, and inhibition by glucocorticoids"; Biochem. J.; 1997; vol. 328; pp. 707-715.

(Continued)

*Primary Examiner*—Barbara P Badio
(74) *Attorney, Agent, or Firm*—James P. Riek

(57) ABSTRACT

The present invention is directed to compounds of formula (I):

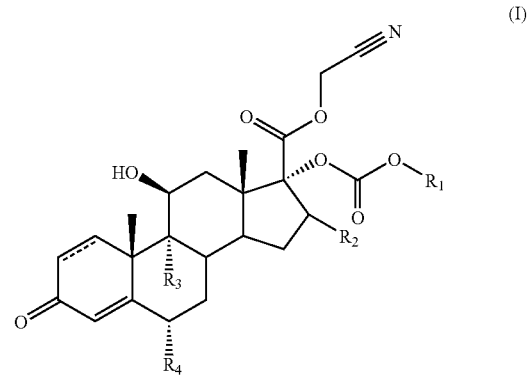

wherein
$R_1$ represents $C_4$-$C_7$ branched alkyl group, a bicycloalkyl group, or a $C_5$-$C_6$ cycloalkyl which optionally may be substituted with a $C_1$-$C_4$ alkyl group;
$R_2$ represents hydrogen, a methyl group, which may be in either the α or β configuration, or a methylene group;
$R_3$ and $R_4$ are the same or a different group and each independently represents hydrogen, halogen or a methyl group;
==== represents a single or a double bond;
and physiologically acceptable solvates thereof, physiologically functional derivatives thereof, pharmaceutical compositions comprising the compounds, the use of the compounds for the manufacture of medicaments particularly for the treatment of inflammatory and/or allergic conditions, processes for the preparation of the compounds, and chemical intermediates in the processes for the manufacture of the compounds.

21 Claims, No Drawings

FOREIGN PATENT DOCUMENTS

| | | |
|---|---|---|
| WO | 0116128 A1 | 3/2001 |
| WO | 0142193 A1 | 6/2001 |
| WO | 0200679 A2 | 1/2002 |
| WO | 0202565 A2 | 1/2002 |
| WO | 0226722 A1 | 4/2002 |
| WO | 0240030 A1 | 5/2002 |
| WO | 0250021 A1 | 6/2002 |
| WO | 02066422 A1 | 8/2002 |
| WO | 02070490 A1 | 9/2002 |
| WO | 02076933 A1 | 10/2002 |
| WO | 03008277 A2 | 1/2003 |
| WO | 03024439 A1 | 3/2003 |
| WO | 03042160 A1 | 5/2003 |
| WO | 03059899 A1 | 7/2003 |
| WO | 03061651 A1 | 7/2003 |
| WO | 03072539 A1 | 9/2003 |
| WO | 03082280 A1 | 10/2003 |
| WO | 03082787 A1 | 10/2003 |
| WO | 03082827 A1 | 10/2003 |
| WO | 03086294 A2 | 10/2003 |
| WO | 03091204 A1 | 11/2003 |
| WO | 03101932 A2 | 12/2003 |
| WO | 03104195 A1 | 12/2003 |
| WO | 2004005229 A1 | 1/2004 |
| WO | 2004009016 A2 | 1/2004 |
| WO | 2004009017 A2 | 1/2004 |
| WO | 2004016578 A2 | 2/2004 |
| WO | 2004018429 A2 | 3/2004 |
| WO | 2004022547 A1 | 3/2004 |
| WO | 2004024728 A2 | 3/2004 |
| WO | 2004026248 A2 | 4/2004 |
| WO | 2004037768 A2 | 5/2004 |
| WO | 2004037773 A1 | 5/2004 |
| WO | 2004037807 A3 | 5/2004 |
| WO | 2004039762 A1 | 5/2004 |
| WO | 2004039766 A1 | 5/2004 |
| WO | 2004056823 A1 | 7/2004 |
| WO | 2004103998 A1 | 7/2004 |
| WO | 2005005451 A1 | 1/2005 |

OTHER PUBLICATIONS

Landells et al.; "Oral Administration of the Phosphodiesterase (PDE)4 Inhibitor, V11294A Inhibits Ex-Vivo Agonist-Induced Cell Activation" (Annu Cong Eur Resp Soc, Sep. 22, 1998); Eur. Respir. J.; 1998; vol. 12 (Suppl. 28); Abstract P2393, p. 362s.

Phillipps et al.; "Synthesis and Structure—Activity Relationships in a Series of Antiinflammatory Corticosteroid Analogues, Halomethyl Androstane -17beta-carbothioates and -17beta-carboselenoates"; J. Med. Chem.; 1994; vol. 37; pp. 3717-3729.

Rachwal et al.; "Chemistry of loteprednol etabonate and related steroids. II. Reactions at ring C and NMR structural studies of the resulting compounds"; Steroids; 1998; vol. 63, No. 4; pp. 193-201.

Austin et al.; "Mometasone furoate is a less specific glucocorticoid than fluticasone propionate"; Eur. Respir. J.; 2002; vol. 20; pp. 1386-1392.

Ueno et al.; "Synthesis and eveluation of antiinflammatory activities of a series of corticosteroid 17.alpha.-esters containing a functional group"; J. Med. Chem.; 1991; vol. 34, No. 8; pp. 2468-2473.

Fujii et al.; "Novel Phosphodiesterase 4 Inhibitor T-440 Reverses and Prevents Human Bronchial Contraction Induced by Allergen"; J. Pharmacol. Exp. Ther.; 1998; vol. 284, No. 1; pp. 162-169.

Souillac et al.; "Characterization of Delivery Systems, Differential Scanning Calorimetry"; Encyclopedia of Controlled Drug Delivery; 1999; pp. 212-227.

Vippagunta et al.; "Crystalline Solids"; Advanced Drug Delivery Reviews; 2001; vol. 48; pp. 3-26.

Druzgala et al.; "Soft Drugs—10. Blanching Activity and Receptor Binding Affinity of a New Type of Glucocorticoid: Loteprednol Etabonate"; J. Steroid Biochem. Molec. Biol.; 1991; vol. 38, No. 2; pp. 149-154.

Szelenyi et al.; "Loteprednol etabonate: a soft steroid for the treatment of allergic diseases of the airways"; Drugs of Today; 2000; vol. 36, No. 5; pp. 313-320.

* cited by examiner

ANDROSTANE 17α-CARBONATE DERIVATIVES FOR USE IN THE TREATMENT OF ALLERGIC AND INFLAMMATORY CONDITIONS

CROSS-REFERENCE TO RELATED APPLICATIONS

This application is filed pursuant to 35 USC 371 as a United States National Phase Application of International Patent Application Ser. No. PCT/EP2006/000149 filed on Jan. 9, 2006, which claims priority from 0500405.6 filed on Jan. 10, 2005 and 0518774.5 filed on Sep. 14, 2005 in the United Kingdom.

1. Field of the Invention

The present invention relates to compounds which are glucocorticoid receptor agonists of the androstane series and to processes for their preparation. The present invention also relates to pharmaceutical formulations containing the compounds and to therapeutic uses thereof, particularly for the treatment of inflammatory and allergic conditions.

BACKGROUND OF THE INVENTION

Glucocorticosteroids which have anti-inflammatory properties are known and are widely used for the treatment of inflammatory disorders or diseases such as asthma and rhinitis. Androstane 17α-carbonate compounds said to have anti-inflammatory activity are disclosed in U.S. Pat. No. 4,996,335. Drugs of Today 2000, 36(5), 313-320, discloses loteprednol etabonate for the treatment of allergic diseases of the airway. We have identified a novel series of androstane 17α-carbonate derivatives.

SUMMARY OF THE INVENTION

Thus, according to one aspect of the invention, there is provided a compound of formula (I)

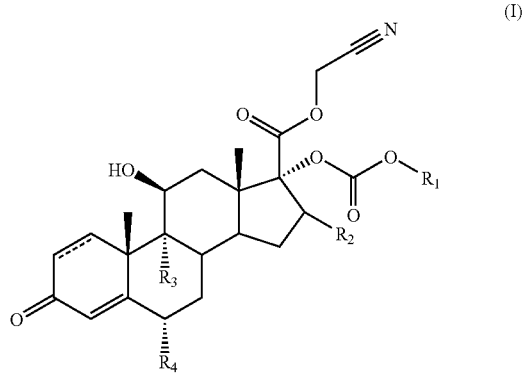

(I)

wherein
$R_1$ represents $C_4$-$C_7$ branched alkyl group, a bicycloalkyl group or a $C_5$-$C_6$ cycloalkyl group which optionally may be substituted with a $C_1$-$C_4$ alkyl group;
$R_2$ represents hydrogen, a methyl group, which may be in either the α or β configuration, or a methylene group;
$R_3$ and $R_4$ are the same or a different group and each independently represents hydrogen, halogen or a methyl group; and ═══ represents a single or a double bond;

or a physiologically acceptable solvate thereof.

Examples of solvates include hydrates.

References hereinafter to a compound according to the invention includes both compounds of formula (I) and solvates thereof.

In some embodiments of the present invention preferred examples of $C_4$-$C_7$ branched alkyl groups which $R_1$ may represent include a 1,1-dimethylethyl, 1-ethylpropyl, 1,1-dimethylpropyl, 2,2-dimethylpropyl, 1,2-dimethylpropyl, 1-ethyl-2-methylpropyl, 2-methyl-1-(1-methylethyl)propyl, 2-ethylbutyl, 1-propylbutyl or a 1-(1-methylethyl)butyl group.

In other embodiments of the present invention preferred examples of $C_4$-$C_7$ branched alkyl groups which $R_1$ may represent include a 1,1-dimethylethyl, 1-ethylpropyl, 1,1-dimethylpropyl, 2,2-dimethylpropyl, 1,2-dimethylpropyl, 1-ethyl-2-methylpropyl, 2-methyl-1-(1-methylethyl)propyl or a 2-ethylbutyl group.

A preferred example of a bicycloalkyl group which $R_1$ may represent is a (1RS,2SR,4SR)-bicyclo[2.2.1]hept-2-yl group.

Preferred examples of bicycloalkyl groups which $R_1$ may represent include a (1RS,2RS,4SR)-bicyclo[2.2.1]hept-2-yl, (1RS,2SR,4SR)-bicyclo[2.2.1]hept-2-yl, (1S,2R,4S)-1,7,7-trimethylbicyclo[2.2.1]hept-2-yl or a (1R,2S,4R)-1,7,7-trimethylbicyclo[2.2.1]hept-2-yl group.

In one embodiment $R_1$ represents a $C_5$-$C_6$ cycloalkyl group which optionally may be substituted with a $C_1$-$C_3$ alkyl group.

Preferred examples of optionally substituted $C_5$-$C_6$ cycloalkyl groups which $R_1$ may represent include a cyclopentyl, (1SR,2RS)-2-methylcyclohexyl or a 4-(1-methylethyl)cyclohexyl group.

Preferred examples of optionally substituted $C_5$-$C_6$ cycloalkyl groups which $R_1$ may represent include a cyclopentyl, (1SR,2RS)-2-methylcyclohexyl, 4-(1-methylethyl)cyclohexyl, trans-4-ethylcyclohexyl or a cis-4-ethylcyclohexyl group.

In some embodiments of the present invention more preferred groups that $R_1$ may represent include a 1,1-dimethylethyl, 1,1-dimethylpropyl, 1-ethylpropyl, 2-methyl-1-(1-methylethyl)propyl, 2,2-dimethylpropyl, (1SR,2RS)-2-methylcyclohexyl, 4-(1-methylethyl)cyclohexyl Isomer B, (1RS,2RS,4SR)-bicyclo[2.2.1]hept-2-yl or a (1RS,2SR,4SR)-bicyclo[2.2.1]hept-2-yl group.

In other embodiments of the present invention more preferred groups that $R_1$ may represent include a 1,1-dimethylethyl, 1,1-dimethylpropyl, 1-ethylpropyl, 2-methyl-1-(1-methylethyl)propyl, 2,2-dimethylpropyl, (1SR,2RS)-2-methylcyclohexyl, 4-(1-methylethyl)cyclohexyl or a (1RS,2SR,4SR)-bicyclo[2.2.1]hept-2-yl group.

Most preferred groups that $R_1$ may represent include a 1,1-dimethylpropyl, 1,1-dimethylethyl or a (1RS,2SR,4SR)-bicyclo[2.2.1]hept-2-yl group.

Most preferred groups that $R_1$ may represent include a 1,1-dimethylpropyl group or a 1,1-dimethylethyl group We prefer $R_2$ to represent a methyl group, especially methyl in the α-configuration.

Compounds of formula (I) in which $R_3$ and $R_4$, which can be the same or different, each represents hydrogen, methyl, fluorine or chlorine, particularly hydrogen or fluorine are preferred. Especially preferred are compounds in which $R_3$ and $R_4$ are both fluorine.

Preferably, ═══ represents a double bond.

It is to be understood that the present invention covers all combinations of preferred groups referred to hereinabove.

Compounds of formula (I) include:

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate;

Cyanomethyl (6α,11β,16α,17α)-17-({[(2-ethylbutyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1-ethyl-2-methylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,2-dimethylpropyl)oxy]carbonyl}oxy)-6,9-difluoro-11-hydroxy-16-methyl-3-oxoandrosta-1,4-diene-17-carboxylate; and Cyanomethyl (6α,11β,16α,17α)-17-{[(cyclopentyloxy)carbonyl]oxy}-6,9-difluoro-11-hydroxy-16-methyl-3-oxoandrosta-1,4-diene-17-carboxylate.

Cyanomethyl (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylate;

Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate;

Cyanomethyl (6α,11β,16α,17α)-7-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-7-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-[({[(1R,2R,3R,5S)-2,6,6-trimethylbicyclo[3.1.1]hept-3-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-[({[(1S,2S,3S,5R)-2,6,6-trimethylbicyclo[3.1.1]hept-3-yl]oxy}carbonyl)oxy]androsta-1,4-diene-17-carboxylate Cyanomethyl (6α,11β,16α,17α)-6,9-difluoro-11-hydroxy-16-methyl-3-oxo-17-[({[(1R,2R,4S)-1,3,3-trimethylbicyclo[2.2.1]hept-2-yl]oxy}carbonyl)oxy]androsta-1,4-diene-17-carboxylate; Cyanomethyl (6α,11β,16α,17α)-17-({[(trans-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(cis-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-3-oxo-17-({[(1-propylbutyl)oxy]carbonyl}oxy)androsta-1,4-diene-17-carboxylate;

Cyanomethyl (6α,11β,16α,17α)-6,9-difluoro-11-hydroxy-16-methyl-3-oxo-17-[({[(1R,2R,4R)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-[({[(1S,2S,4S)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-({[(1,2,2-trimethylpropyl)oxy]carbonyl}oxy)androsta-1,4-diene-17-carboxylate; and Cyanomethyl (6α,11β,16α,17α)-6,9-difluoro-11-hydroxy-16-methyl-17-[({[1-(1-methylethyl)butyl]oxy}carbonyl)oxy]-3-oxoandrosta-1,4-diene-17-carboxylate.

In some embodiments of the present invention preferred compounds of formula (I) include:

Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate;

Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate;

Cyanomethyl (6α,11β,16α,17α)-17-({[(2-ethylbutyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylate;

Cyanomethyl (6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1-ethyl-2-methylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,2-dimethylpropyl)oxy]carbonyl}oxy)-6,9-difluoro-11-hydroxy-16-methyl-3-oxoandrosta-1,4-diene-17-carboxylate; and Cyanomethyl (6α,11β,16α,17α)-7-{[(cyclopentyloxy)carbonyl]oxy}-6,9-difluoro-11-hydroxy-16-methyl-3-oxoandrosta-1,4-diene-17-carboxylate.

In other embodiments of the present invention preferred compounds of formula (I) include:

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate;

Cyanomethyl (6α,11β,16α,17α)-17-({[(2-ethylbutyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1-ethyl-2-methylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,2-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-{[(cyclopentyloxy)carbonyl]oxy}-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylate;

Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate;

Cyanomethyl (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylate;

Cyanomethyl (6α,11β,16α,17α)-17-({[(trans-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(cis-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-3-oxo-17-({[(1-propylbutyl)oxy]carbonyl}oxy)androsta-1,4-diene-17-carboxylate; and Cyanomethyl (6α,11β,16α,17α)-6,9-difluoro-11-hydroxy-16-methyl-17-[({[1-(1-methylethyl)butyl]oxy}carbonyl)oxy]-3-oxoandrosta-1,4-diene-17-carboxylate.

More preferred compounds of formula (I) are:

Cyanomethyl (6α,11β,16α,17α)-7-({[(1,1-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate;

Cyanomethyl (6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylate;

Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate Isomer B;

Cyanomethyl (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate; and Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate.

In some embodiments of the present invention most preferred compounds include:

Cyanomethyl (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate; and Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate In other embodiments of the present invention most preferred compounds are:

Cyanomethyl (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylate; and Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate.

The compounds of formula (I) have potentially beneficial anti-inflammatory or anti-allergic effects, particularly upon topical administration, demonstrated by, for example, their ability to bind to the glucocorticoid receptor and to illicit a response via that receptor. Hence, the compounds of formula (I) are potentially useful in the treatment of inflammatory and/or allergic disorders.

Examples of disease states in which the compounds of the invention may have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) may be useful in human or veterinary medicine, in particular as anti-inflammatory and anti-allergic agents.

There is thus provided as a further aspect of the invention a compound of formula (I) or a physiologically acceptable solvate thereof for use in human or veterinary medicine, particularly in the treatment of patients with inflammatory and/or allergic conditions.

According to another aspect of the invention, there is provided the use of a compound of formula (I) or a physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a compound of formula (I) or physiologically acceptable solvate thereof.

The compounds according to the invention may be formulated for administration in any convenient way, and the invention therefore also includes within its scope pharmaceutical compositions comprising a compound of formula (I) or physiologically acceptable solvate thereof together, if desirable, in admixture with one or more physiologically acceptable diluents or carriers.

Further, there is provided a process for the preparation of such pharmaceutical compositions which comprises mixing the ingredients.

The compounds according to the invention may, for example, be formulated for oral, intranasal, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol.

Advantageously, the formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 20 μg-10 mg of the compound of formula (I). Alternatively, the compound of the invention may be presented without excipients such as lactose.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will be within the range of from 0.1 to 5%.

Aerosol formulations are preferably arranged so that each metered dose or "puff" of aerosol contains 20 μg-2000 μg, preferably about 20 μg-500 μg of a compound of formula (I). Administration may be once daily or several times daily, for example 2, 3, 4 or 8 times, giving for example 1, 2 or 3 doses each time. The overall daily dose with an aerosol will be within the range 100 μg-10 mg preferably, 200 μg-2000 μg. The overall daily dose and the metered dose delivered by capsules and cartridges in an inhaler or insufflator will generally be double those with aerosol formulations.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compounds of the invention.

The compounds according to the invention may in general be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5-30 mg, dependent on the condition being treated, and the duration of treatment desired.

Slow release or enteric coated formulations may be advantageous, particularly for the treatment of inflammatory bowel disorders.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example another corticosteroid or an NSAID), an anticholinergic agent, a $\beta_2$-adrenoreceptor agonist, an antiinfective agent (e.g. an antibiotic or an antiviral), or an antihistamine. Combinations comprising a compound of formula (I) or a pharmaceutically acceptable salt, solvate or physiologically functional derivative thereof together with a $\beta_2$-adrenoreceptor agonist, and/or an anticholinergic, and/or a PDE-4 inhibitor are preferred. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

A combination comprising of compound of the invention together with a $\beta_2$-adrenoreceptor agonist is particularly preferred.

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period.

Further examples of $\beta_2$-adrenoreceptor agonists include carmoterol, etanterol, naminterol, clenbuterol, pirbuterol, flerobuterol, reproterol, bambuterol, indacaterol and salts thereof.

Preferred $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Especially preferred $\beta_2$-adrenoreceptor agonists include compounds of formula (XX):

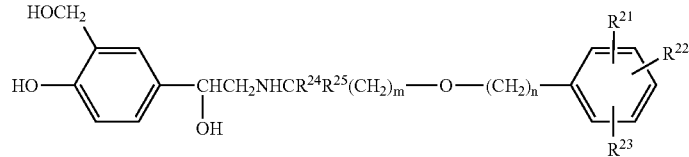

(XX)

or a salt or solvate thereof, wherein:

m is an integer of from 2 to 8;

n is an integer of from 3 to 11, with the proviso that m+n is 5 to 19, $R^{21}$ is —$XSO_2NR^{26}R^{27}$ wherein X is —$(CH_2)_p$— or $C_{2-6}$ alkenylene;

$R^{26}$ and $R^{27}$ are independently selected from hydrogen, $C_{1-6}$alkyl, $C_{3-7}$cycloalkyl, $C(O)NR^{28}R^{29}$, phenyl, and phenyl ($C_{1-4}$alkyl)-, or $R^{26}$ and $R^{27}$, together with the nitrogen to which they are bonded, form a 5-, 6-, or 7-membered nitrogen containing ring, and $R^{26}$ and $R^{27}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^{28}$, —$SO_2NR^{28}R^{29}$, —$CONR^{28}R^{29}$, —$NR^{28}C(O)R^{29}$, or a 5-, 6- or 7-membered heterocylic ring;

$R^{28}$ and $R^{29}$ are independently selected from hydrogen, $C_{1-6}$alkyl, $C_{3-6}$cycloalkyl, phenyl, and phenyl ($C_{1-4}$alkyl)-; and p is an integer of from 0 to 6, preferably from 0 to 4;

$R^{22}$ and $R^{23}$ are independently selected from hydrogen, $C_{1-6}$alkyl, $C_{1-6}$alkoxy, halo, phenyl, and $C_{1-6}$haloalkyl; and $R^{24}$ and $R^{25}$ are independently selected from hydrogen and $C_{1-4}$alkyl with the proviso that the total number of carbon atoms in $R^{24}$ and $R^{25}$ is not more than 4.

Especially preferred $\beta_2$-adrenoreceptor agonists include:

3-(4-{[6-({(2R)-2-hydroxy-2-[4-hydroxy-3-(hydroxymethyl)phenyl]ethyl}amino)hexyl]oxy}butyl)benzenesulfonamide;

3-(3-{[7-({(2R)-2-hydroxy-2-[4-hydroxy-3-hydroxymethyl)phenyl]ethyl}-amino)heptyl]oxy}propyl)benzenesulfonamide;

4-{(1R)-2-[(6-{2-[(2,6-dichlorobenzyl)oxy]ethoxy}hexyl) amino]-1-hydroxyethyl}-2-(hydroxymethyl)phenol;

4-{(1R)-2-[(6-{4-[3-(cyclopentylsulfonyl)phenyl] butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

Suitable anti-inflammatory agents include corticosteroids. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-hydroxy-16α-methyl-17α-[(4-methyl-1,3-thiazole-5-carbonyl)oxy]-3-oxo-androsta-1,4-diene-171-carbothioic acid S-fluoromethyl ester, 6α,9α-difluoro-17u.-[(2-furanylcarbonyl)oxy]-11-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (eg. the 17-propionate ester or the 17,21-dipropionate ester), budesonide, flunisolide, mometasone esters (eg. the furoate ester), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-171-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-171-carbothioic acid S-fluoromethyl ester. Further examples of corticosteroids include 6α,9α-difluoro-11β-hydroxy-16α-methyl-3-oxo-17α-(2,2,3,3-tetramethycyclopropylcarbonyl)oxy-androsta-1,4-diene-171-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester.

Non-steroidal compounds having glucocorticoid agonism that may possess selectivity for transrepression over transactivation and that may be useful in combination therapy include those covered in the following patents: WO03/082827, WO01/10143, WO98/54159, WO04/005229, WO04/009016, WO04/009017, WO04/018429, WO03/104195, WO03/082787, WO03/082280, WO03/059899, WO03/101932, WO02/02565, WO01/16128, WO0066590, WO03/086294, WO04/026248, WO03/061651, WO03/08277.

Suitable anti-inflammatory agents include non-steroidal anti-inflammatory drugs (NSAID's).

Suitable NSAID's include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis (eg. montelukast), iNOS inhibitors, tryptase and elastase inhibitors, beta-2 integrin antagonists and adenosine receptor agonists or antagonists (e.g. adenosine 2a agonists), cytokine antagonists (e.g. chemokine antagonists, such as a CCR3 antagonist) or inhibitors of cytokine synthesis, or 5-lipoxygenase inhibitors. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

Of particular interest is use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds of interest include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds of interest are disclosed in the published international patent application WO04/024728 (Glaxo Group Ltd), PCT/EP2003/014867 (Glaxo Group Ltd) and PCT/EP2004/005494 (Glaxo Group Ltd).

Suitable anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (e.g. as the bromide, CAS 22254-24-6, sold under the name Atrovent), oxitropium (e.g. as the bromide, CAS 30286-75-0) and tiotropium (e.g. as the bromide, CAS 136310-93-5, sold under the name Spiriva). Also of interest are revatropate (e.g. as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (e.g. as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other suitable anticholinergic agents include compounds of formula (XXI), which are disclosed in U.S. patent application 60/487,981:

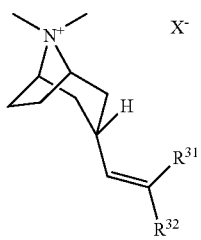

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

X⁻ represents an anion associated with the positive charge of the N atom. X⁻ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further suitable anticholinergic agents include compounds of formula (XXII) or (XXIII), which are disclosed in U.S. patent application 60/511,009:

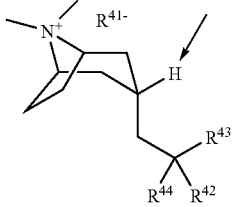

(XXII)

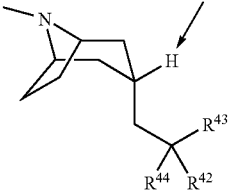

(XXIII)

wherein:

the H atom indicated is in the exo position;

$R^{41}$ represents an anion associated with the positive charge of the N atom. $R^{41}$ may be but is not limited to chloride, bromide, iodide, sulfate, benzene sulfonate and toluene sulfonate;

$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;

$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —OR$^{45}$, —CH$_2$OR$^{45}$, —CH$_2$OH, —CN, —CF$_3$, —CH$_2$O(CO)R$^{46}$, —CO$_2$R$^{47}$, —CH$_2$NH$_2$, —CH$_2$N(R$^{47}$)SO$_2$R$^{45}$, —SO$_2$N(R$^{47}$)(R$^{48}$), —CON(R$^{47}$)(R$^{41}$), —CH$_2$N(R$^{48}$)CO(R$^{46}$), —CH$_2$N(R$^{48}$)SO$_2$(R$^{46}$), —CH$_2$N(R$^{48}$)CO$_2$(R$^{45}$), —CH$_2$N(R$^{48}$)CONH(R$^{47}$);

$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;

$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;

$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:

(Endo)-3-(2-methoxy-2,2-di-thiophen-2-yl-ethyl)-8,8-dimethyl-8-azonia-bicyclo[3.2.1]octane iodide;

3-((Endo)-8-methyl-8-aza-bicyclo[3.2.1]oct-3-yl)-2,2-diphenyl-propionitrile;

(Endo)-8-methyl-3-(2,2,2-triphenyl-ethyl)-8-aza-bicyclo[3.2.1]octane;

3-((Endo)-8-methyl-8-aza-bicyclo[3.2.1]oct-3-yl)-2,2-diphenyl-propionamide;

3-((Endo)-8-methyl-8-aza-bicyclo[3.2.1]oct-3-yl)-2,2-diphenyl-propionic acid;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
3-((Endo)-8-methyl-8-aza-bicyclo[3.2.1]oct-3-yl)-2,2-diphenyl-propan-1-ol;
N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8-dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]-urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

More preferred compounds useful in the present invention include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;
(Endo)-3-(2-cyano-2,2-di-thiophen-2-yl-ethyl)-8,8-dimethyl-8-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

Suitable antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, e.g diphenylhydramine, pyrilamine, clemastine, chloropheniramine. Second generation antagonists, which are non-sedating, include loratidine, desloratidine, terfenadine, astemizole, acrivastine, azelastine, levocetirizine fexofenadine and cetirizine.

Examples of preferred anti-histamines include loratidine, desloratidine, fexofenadine and cetirizine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a $\beta_2$-adrenorecptor agonist.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a $\beta_2$-adrenoreceptor agonist.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Preferably the individual compounds of such combinations may be administered simultaneously in a combined pharmaceutical combination. Appropriate doses of known therapeutic agents will be readily appreciated by those skilled in the art.

The compounds of formula (I) and solvates thereof may be prepared by the methodology described hereinafter, constituting a further aspect of this invention.

A process according to the invention for preparing a compound of formula (I) comprises reaction of a carboxylic acid of formula (II)

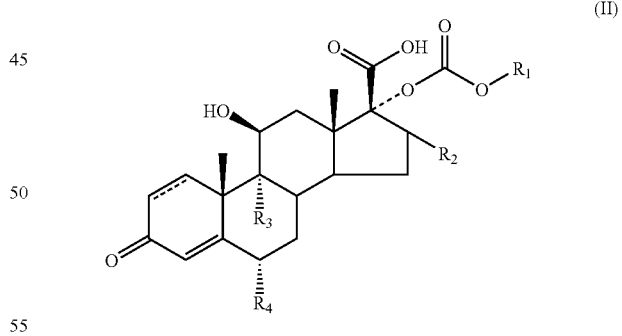

wherein $R_1$, $R_2$, $R_3$, $R_4$ and ==== are as defined above, with a compound of formula L-CH$_2$—CN wherein L represents a leaving group.

In this process the compound of formula (II) may be reacted with a compound of formula L-CH$_2$—CN wherein L represents a leaving group such as halogen atom or a tosyl or mesyl group or the like, under standard conditions. For example the reaction may be performed in an inert polar organic solvent e.g. N,N-dimethylformamide in the presence of a base e.g. potassium carbonate, sodium carbonate.

Compounds of formula (II) may conveniently be employed as salts when such salts may be prepared in crystalline form, or as solvates.

In a further aspect of the present invention, there is provided a compound of formula (II)

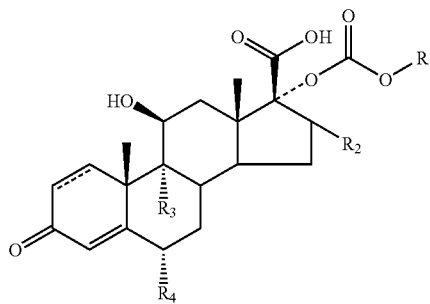

wherein $R_1$, $R_2$, $R_3$, $R_4$ and ≡≡≡ are as defined for compounds of formula (I).

Compounds of formula L-CH$_2$—CN are either known or may be prepared by known methods.

Compounds of formula (II) may be prepared from the corresponding 17α-hydroxyl derivative of formula (III):

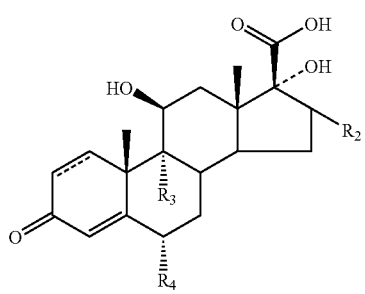

wherein $R_2$, $R_3$, $R_4$ and ≡≡≡ are as defined above, using for example, methodology similar to that described by described by G. H. Phillipps et al., to prepare 17α carboxylate esters (Journal of Medicinal Chemistry, (1994), 37, 3717-3729) and by Druzgala et al., to prepare the 17α carbonate ester loteprednol etabonate (Journal of Steroid Chemistry and Molecular Biology, (1991), 38, 149-154). The step typically comprises the reaction of the hydroxyacid (III) with a chloroformate R$_1$OCOCl, or anhydride (R$_1$OCO)$_2$O, in the presence of a mild base e.g. triethylamine in a suitable solvent e.g. dichloromethane. In the case of sterically encumbered R$_1$ groups anhydrides (R$_1$OCO)$_2$O may be preferred to the chloroformates.

Generally the chloroformate or anhydride would be employed in at least 2 times molar quantity relative to the compound of formula (III). The second mole of chloroformate or anhydride tends to react with the carboxylic acid moiety in the compound of formula (III) and would need to be removed by reaction with an amine such as diethylamine or 1-methylpiperazine. The chloroformates are either commercially available or are readily prepared by standard methodology e.g. by reaction of the corresponding alcohol R$_{10}$H with phosgene or more preferably triphosgene in the presence of a base e.g. pyridine in a suitable solvent e.g. dichloromethane.

More conveniently, reaction of the 17α-hydroxyl derivative (III) with the chloroformate R$_1$OCOCl or anhydride (R$_1$O CO)$_2$O in pyridine solution often affords the 17a carbonate (II) directly.

Compounds of formula (III) are either known or may be prepared in accordance with procedures described by G. H. Phillipps et al., Journal of Medicinal Chemistry, (1994), 37, 3717-3729.

The following compounds of formula (II) are new and form an aspect of the invention:

(6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylic acid;

(6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylic acid;

(6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid;

(6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylic acid;

(6α,11β,16α,17α)-17-({[(2-ethylbutyl)oxy]carbonyl}oxy)-6,9-difluoro-11-hydroxy-16-methyl-3-oxoandrosta-1,4-diene-17-carboxylic acid;

(6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylic acid;

(6α,11β,16α,17α)-17-({[(1-ethyl-2-methylpropyl)oxy]carbonyl}oxy)-6,9-difluoro-1-hydroxy-16-methyl-3-oxoandrosta-1,4-diene-17-carboxylic acid;

(6α,11β,16α,17α)-17-({[(1,2-dimethylpropyl)oxy]carbonyl}oxy)-6,9-difluoro-1-hydroxy-16-methyl-3-oxoandrosta-1,4-diene-17-carboxylic acid;

(6α,11β,16α,17α)-17-{[(cyclopentyloxy)carbonyl]oxy}-6,9-difluoro-11-hydroxy-16-methyl-3-oxoandrosta-1,4-diene-17-carboxylic acid;

(6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylic acid;

(6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylic acid;

(6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylic acid; and (6α,11β,16α,17α-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylic acid;

The following compounds of formula (II) are also new and form an aspect of the invention:

(6α,11β,16α,17α)-6,9-difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylic acid;

(6α,11β,16α,17α)-6,9-difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylic acid;

(6α,11β,16α,17α)-6,9-difluoro-11-hydroxy-16-methyl-3-oxo-17-[({[(1R,2R,3R,5S)-2,6,6-trimethylbicyclo[3.1.1]hept-3-yl]oxy}carbonyl)oxy]androsta-1,4-diene-17-carboxylic acid;

(6α,11β,16α,17α)-6,9-difluoro-11-hydroxy-16-methyl-3-oxo-17-[({[(1S,2S,3S,5R)-2,6,6-trimethylbicyclo[3.1.1]hept-3-yl]oxy}carbonyl)oxy]androsta-1,4-diene-17-carboxylic acid;

(6α,11β,16α,17α)-6,9-difluoro-11-hydroxy-16-methyl-3-oxo-17-[({[(1R,2R,4S)-1,3,3-trimethylbicyclo[2.2.1]hept-2-yl]oxy}carbonyl)oxy]androsta-1,4-diene-17-carboxylic acid;

(6α,11β,16α,17α)-17-({[(trans-4-ethylcyclohexyl)oxy]carbonyl}oxy)-6,9-difluoro-11-hydroxy-16-methyl-3-oxoandrosta-1,4-diene-17-carboxylic acid;

(6α,11β,16α,17α)-17-({[(cis-4-ethylcyclohexyl)oxy]carbonyl}oxy)-6,9-difluoro-11-hydroxy-16-methyl-3-oxoandrosta-1,4-diene-17-carboxylic acid;

(6α,11β,16α,17α)-6,9-difluoro-11-hydroxy-16-methyl-3-oxo-17-({[(1-propylbutyl)oxy]carbonyl}oxy)androsta-1,4-diene-17-carboxylic acid;

(6α,11β,16α,17α)-6,9-difluoro-11-hydroxy-16-methyl-3-oxo-17-[({[(1RS,2RS,4RS)-1,7,7-trimethylbicyclo[2.2.1]hept-2-yl]oxy}carbonyl)oxy]androsta-1,4-diene-17-carboxylic acid;

(6α,11β,16α,17α)-6,9-difluoro-11-hydroxy-16-methyl-3-oxo-17-({[(1,2,2-trimethylpropyl)oxy]carbonyl}oxy)androsta-1,4-diene-17-carboxylic acid; and (6α,11β,16α,17α)-6,9-difluoro-11-hydroxy-16-methyl-17-[({[1-(1-methylethyl)butyl]oxy}carbonyl)oxy]-3-oxoandrosta-1,4-diene-17-carboxylic acid.

Compounds of formula (I) and/or solvates thereof demonstrate agonism at the glucocorticoid receptor.

Compounds of formula (I) and/or solvates thereof may demonstrate good anti-inflammatory properties, with predictable pharmacokinetic and pharmacodynamic behaviour. They also may have an attractive side-effect profile, demonstrated, for example, by increased selectivity for the glucocorticoid receptor over the progesterone receptor and/or increased selectivity for glucocorticoid receptor mediated transrepression over transactivation and are likely to be compatible with a convenient regime of treatment in human patients.

The following non-limiting Examples illustrate the invention:

DETAILED DESCRIPTION

EXAMPLES

General

Chromatographic purification was performed using pre-packed Bond Elut silica gel cartridges available commercially from Varian. These cartridges were pre-conditioned with dichloromethane prior to use. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve).

Autopreparative HPLC was carried out using a Waters 600 gradient pump, Waters 2767 inject/collector, Waters Reagent Manager, Micromass ZMD mass spectrometer, Gilson Aspec waste collector and Gilson 115 post-fraction UV detector. The column used was typically a Supelco LCABZ++ column with dimension of 20 mm internal diameter by 100 mm in length. The stationary phase particle size is 5 µm. The flow rate was 20 ml/min and the runtime was 15 minutes, which comprises a 10-minute gradient followed by a 5 minute column flush and re-equilibration step.

Solvent A: Aqueous solvent=water+0.1% formic acid.

Solvent B: Organic solvent=MeCN: water 95:5+0.05% formic acid

Specific gradients used were dependent upon the retention time in the analytical system. For 2.0-2.8 min, 5-30% B, 2.5-3.0 min, 15-55% B, 2.8-4.0 min, 30-80% B and 3.8-5.5 min, 50-90% B.

Intermediates

Intermediate 1: (6α,11β,16α,17α)-17-({[(1,1-Dimethylethyl)oxy]carbonyl}oxy)-6,9-difluoro-11-hydroxy-16-methyl-3-oxoandrosta-1,4-diene-17-carboxylic acid

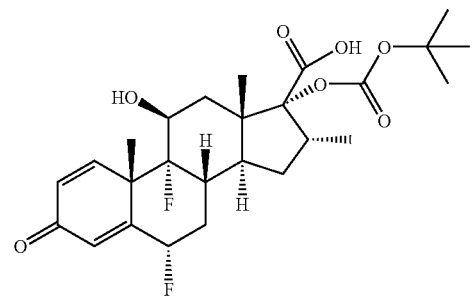

Bis(1,1-dimethylethyl) carbonate (121 mg, 0.56 mmol) was added to a stirred solution of (6α,11β,16α,17α)-6,9-difluoro-11,17-dihydroxy-16-methyl-3-oxoandrosta-1,4-diene-17-carboxylic acid (G. H. Phillipps et al., (1994) Journal of Medicinal Chemistry, 37, 3717-3729) (200 mg, 0.5 mmol) in pyridine (5 ml) and the mixture stirred at room temperature overnight. The solvent was evaporated and the residue was stirred with 2M hydrochloric acid (20 ml) and the resulting precipitate was collected by filtration, washed with water and dried in vacuo at 60° C. to give the title compound: LCMS retention time 3.27 min.

Intermediate 2: (6α,11β,16α,17α)-17-({[(1 ]-Dimethylpropyl)oxy-1-carbonyl}oxy)-6,9-difluoro-11-hydroxy-16-methyl-3-oxoandrosta-1,4-diene-17-carboxylic acid

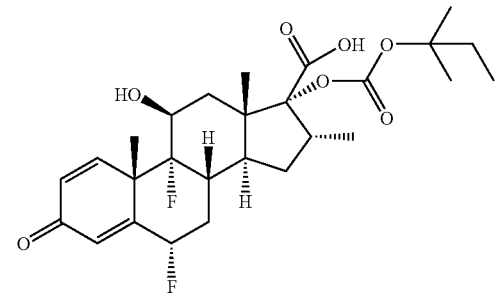

Prepared from bis(1,1-dimethylpropyl) dicarbonate using a method similar to that described for (6α,11β,16α,17α)-17-

({[(1,1-dimethylethyl)oxy]carbonyl}oxy)-6,9-difluoro-11-hydroxy-16-methyl-3-oxoandrosta-1,4-diene-17-carboxylic acid (Intermediate 1). LCMS retention time 3.38 min.

Intermediate 3: (6α,11β,16α,17α)-17-({[(1-Ethylpropyl)oxy]carbonyl}oxy)-6,9-difluoro-11-hydroxy-16-methyl-3-oxoandrosta-1,4-diene-17-carboxylic acid

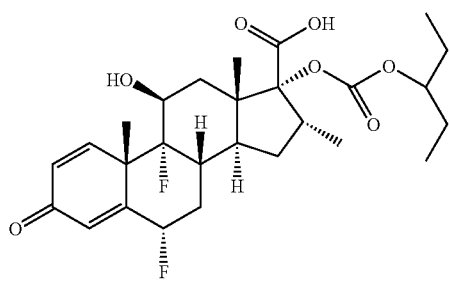

A solution of 3-pentanol (108 μL, 1 mmol) and pyridine (81 g, 1 mmol) in anhydrous dichloromethane (2 ml) was added portionwise over 10 min to a stirred and cooled (ice) solution of triphosgene (98 mg, 0.33 mmol) in anhydrous dichloromethane (4 ml) under nitrogen. After 1 h, approximately half of the resulting chloroformate solution was added to a solution of (6α,11β,16α,17α)-6,9-difluoro-11,17-dihydroxy-16-methyl-3-oxoandrosta-1,4-diene-17-carboxylic acid (200 mg, 0.5 mmol) in pyridine (2 ml) and the mixture stirred at room temperature overnight. The solvent was evaporated and the residue was stirred with 2M hydrochloric acid (10 ml) and the resulting precipitate was collected by filtration, washed with water and dried in vacuo to give the title compound as a white solid (246 mg): LCMS retention time 3.42 min.

Intermediate 4: (6α,11β,16α,17α)-6,9-Difluoro-11-hydroxy-16-methyl-17-[({[2-methyl-1-(1-methylethyl)propyl]oxy}carbonyl)oxy]-3-oxoandrosta-1,4-diene-17-carboxylic acid

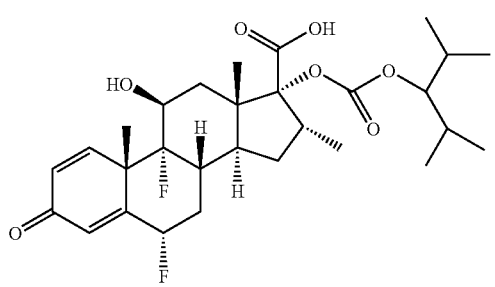

Prepared from 2,4-dimethyl-3-pentanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.58 min.

Intermediate 5: (6α,11β,16α,17α)-17-({[(2-Ethylbutyl)oxy]carbonyl}oxy)-6,9-difluoro-11-hydroxy-16-methyl-3-oxoandrosta-1,4-diene-17-carboxylic acid

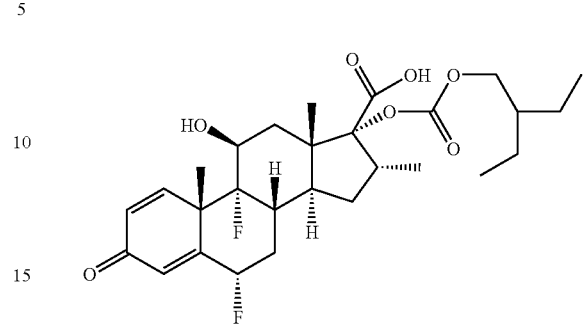

Prepared from 2-ethyl-1-butanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.63 min.

Intermediate 6: (6α,11β,16α,17α)-17-({[(2,2-Dimethylpropyl)oxy]carbonyl}oxy)-6,9-difluoro-11-hydroxy-16-methyl-3-oxoandrosta-1,4-diene-17-carboxylic acid

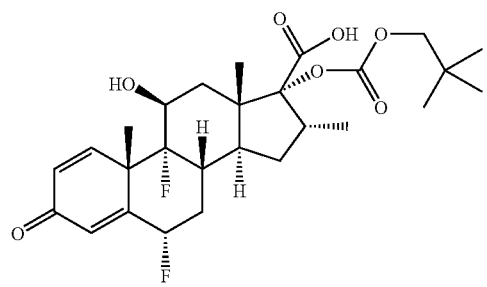

Prepared from 2,2-dimethyl-1-propanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.47 min.

Intermediate 7: (6(.,11β,16α,17α)-17-({[(1-Ethyl-2-methylpropyl)oxy]carbonyl}oxy)-6,9-difluoro-11-hydroxy-16-methyl-3-oxoandrosta-1,4-diene-17-carboxylic acid

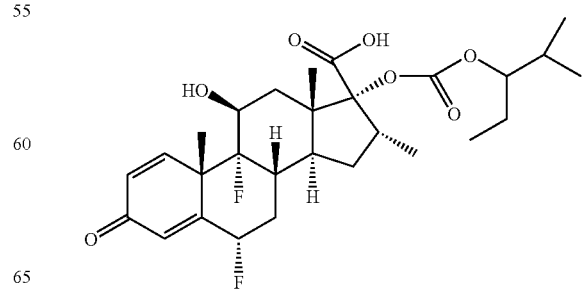

Prepared from 2-methyl-3-pentanol using a method similar to that described for (6α,11β,16α,17α)-17-({[(1-Ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.54 min.

Intermediate 8: (6α,11β,16α,17α)-17-({[(1,2-Dimethylpropyl)oxy]carbonyl}oxy)-6,9-difluoro-11-hydroxy-16-methyl-3-oxoandrosta-1,4-diene-17-carboxylic acid

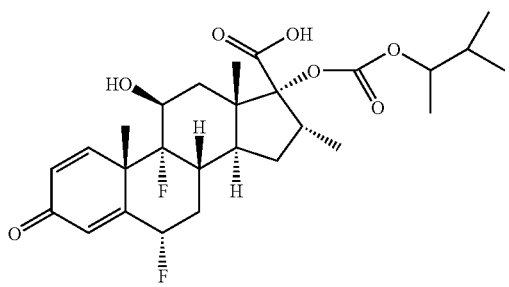

Prepared from 3-methyl-2-butanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.43 min.

Intermediate 9: (6α,11β,16α,17α)-17-{[(Cyclopentyloxy)carbonyl]oxy}-6,9-difluoro-11-hydroxy-16-methyl-3-oxoandrosta-1,4-diene-17-carboxylic acid

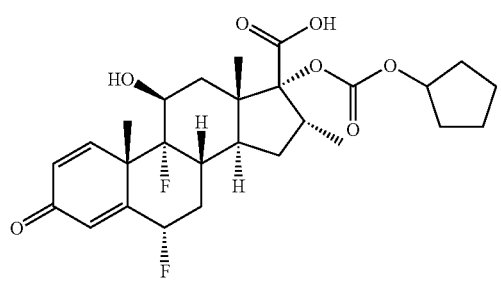

A solution of cyclopentyl chloroformate (268 mg, 1.8 mmol) in dry dichloromethane (2 ml) was added to a stirred and cooled (ice) solution of (6α,11β,16α,17α)-6,9-difluoro-11,17-dihydroxy-16-methyl-3-oxoandrosta-1,4-diene-17-carboxylic acid (298 mg, 0.75 mmol) and triethylamine (0.21 ml, 1.5 mmol) in dry dichloromethane (5 ml) and the mixture stirred for 2 h in ice and then overnight at room temperature. The mixture was washed successively with aqueous sodium bicarbonate, 1M hydrochloric acid and water (30 ml of each) and then dried through a hydrophobic frit and evaporated. The residue was dissolved in 1,4-dioxan (10 ml) and treated with N-methyl piperazine (200 mg, 2 mmol) and the mixture stirred at room temperature until the reaction was shown to be complete by LCMS. The mixture was added portionwise to stirred and cooled (ice) 2M hydrochloric acid and the precipitated product was collected, washed with water and dried in vacuo to give the title compound (31 mg): LCMS retention time 3.36 min.

Intermediate 10: (6α,11β,16α,17α)-6,9-Difluoro-11-hydroxy-16-methyl-17-[({[(1SR,2RS)-2-methylcyclohexyl]oxy}carbonyl)oxy]-3-oxoandrosta-1,4-diene-17-carboxylic acid

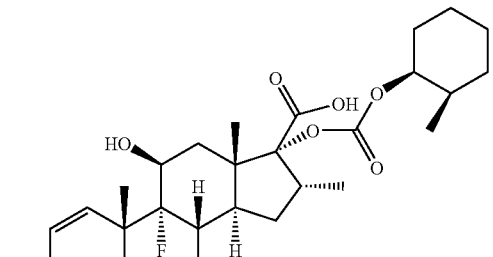

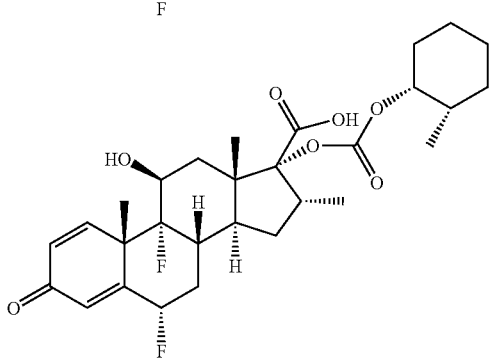

Prepared from racemic cis-2-methylcyclohexanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.62 min.

Intermediate 11: (6α,11β,16α,17α)-6,9-Difluoro-11-hydroxy-16-methyl-17-[({[4-(1-methylethyl)cyclohexyl]oxy}carbonyl)oxy]-3-oxoandrosta-1,4-diene-17-carboxylic acid

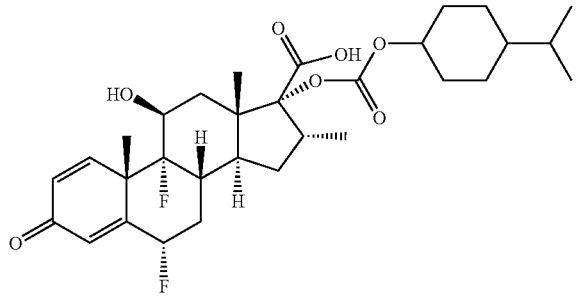

Prepared from cis/trans-4-(1-methylethyl)cyclohexanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.87 min.

Intermediate 12: (6α,11β,16α,17α)-17-([{(1RS,2RS,4SR)-Bicyclo[2.2.1]hept-2-yloxy]carbonyl}oxy)-6,9-difluoro-11-hydroxy-16-methyl-3-oxoandrosta-1,4-diene-17-carboxylic acid

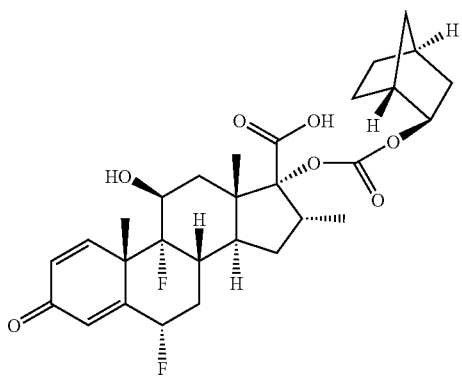

Prepared from racemic exo-2-norborneol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.54 min.

Intermediate 13: (6α,11β,16α,17α)-17-({[(1RS,2SR,4SR)-Bicyclo[2.2.1]hept-2-yloxy]carbonyl}oxy)-6,9-difluoro-11-hydroxy-16-methyl-3-oxoandrosta-1,4-diene-17-carboxylic acid

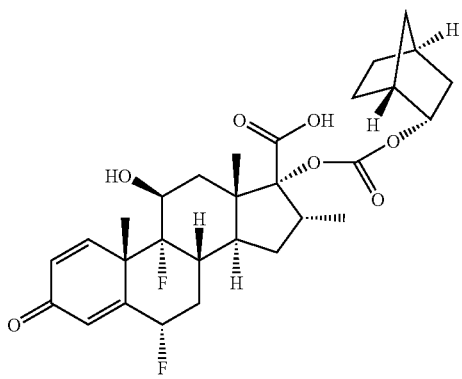

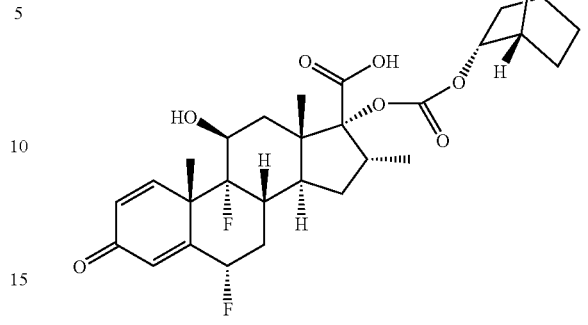

Prepared from racemic endo-2-norborneol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.54 min.

Intermediate 14: (6α,11β,16α,17α)-6,9-Difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylic acid

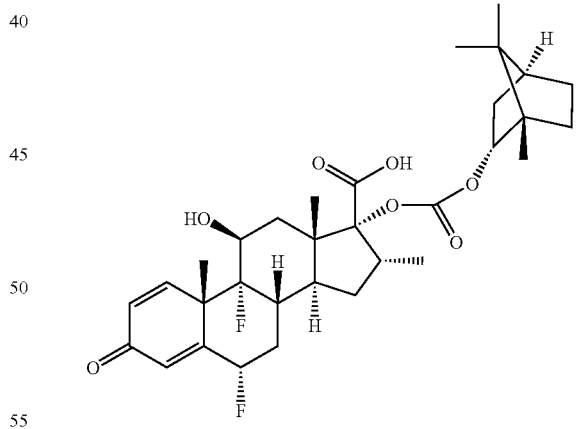

Prepared from (−) borneol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.87 min.

Intermediate 15: (6α,11β,16α,17α)-6,9-Difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylic acid

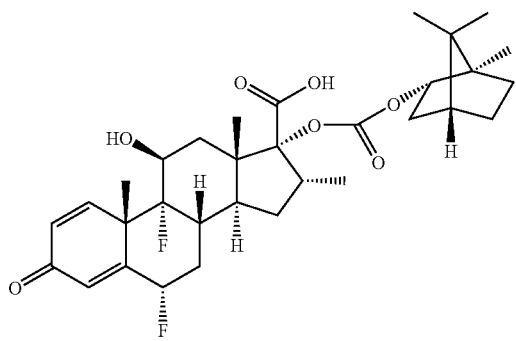

Prepared from (+) borneol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.81 min.

Intermediate 16: (6α,11β,16α,17α)-6,9-Difluoro-11-hydroxy-16-methyl-3-oxo-17-[({[(1R,2R,3R,5S)-2,6,6-trimethylbicyclo[3.1.1]hept-3-yl]oxy}carbonyl)oxy]androsta-1,4-diene-17-carboxylic acid

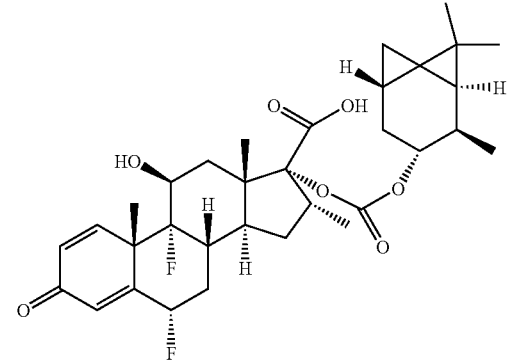

Prepared from (−) isopinocampheol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.87 min.

Intermediate 17: (6α,11β,16α,17α)-6,9-Difluoro-11-hydroxy-16-methyl-3-oxo-17-[({[(1S,2S,3S,5R)-2,6,6-trimethylbicyclo[3.1.1]hept-3-yl]oxy}carbonyl)oxy]androsta-1,4-diene-17-carboxylic acid

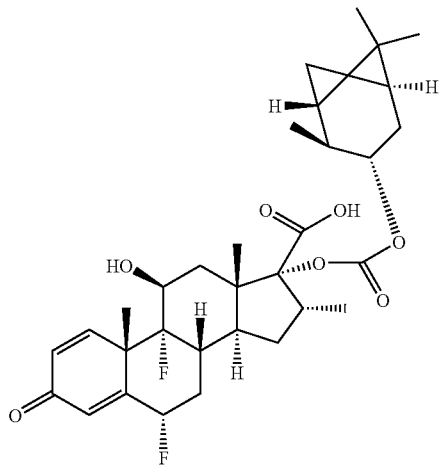

Prepared from (+)-isopinocampheol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.86 min.

Intermediate 18: (6α,11β,16α,17α)-6,9-Difluoro-11-hydroxy-16-methyl-3-oxo-17-[({[(1R,2R,4S)-1,3,3-trimethylbicyclo[2.2.1]hept-2-yl]oxy}carbonyl)oxy]androsta-1,4-diene-17-carboxylic acid

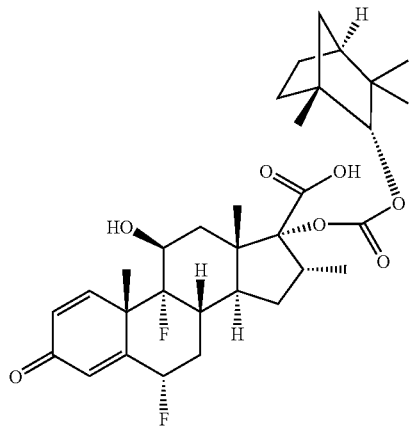

Prepared from (1R)-endo-(+)-fenchyl alcohol using a method similar to that described for (6α,11β,16α,17α-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.87 min.

Intermediate 19: (6α,11β,16α,17α)-17-({[(trans-4-Ethylcyclohexyl)oxy]carbonyl}oxy)-6,9-difluoro-11-hydroxy-16-methyl-3-oxoandrosta-1,4-diene-17-carboxylic acid

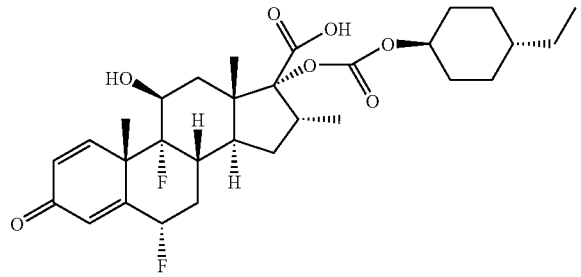

Prepared from trans-4-ethylcyclohexanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.78 min.

Intermediate 20: (6α,11β,16α,17α)-17-({[(cis-4-Ethylcyclohexyl)oxy]carbonyl}oxy)-6,9-difluoro-11-hydroxy-16-methyl-3-oxoandrosta-1,4-diene-17-carboxylic acid

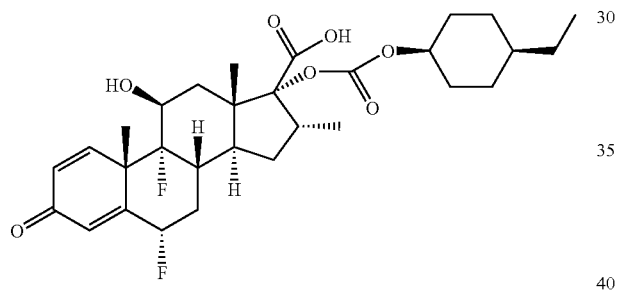

Prepared from cis-4-ethylcyclohexanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.76 min.

Intermediate 21: (6α,11β,16α,17α)-6,9-Difluoro-11-hydroxy-16-methyl-3-oxo-17-({[(1-propylbutyl)oxy]carbonyl}oxy)androsta-1,4-diene-17-carboxylic acid

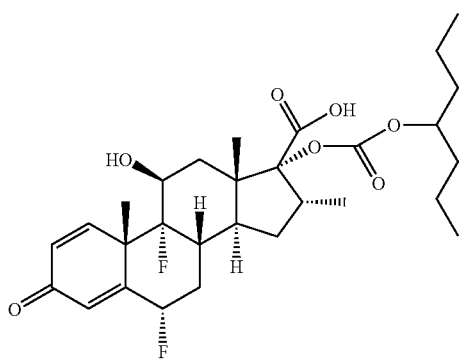

Prepared from 4-heptanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.65 min.

Intermediate 22: (6α,11β,16α,17α)-6,9-Difluoro-11-hydroxy-16-methyl-3-oxo-17-[({[(1RS,2RS,4RS)-1,7,7-trimethylbicyclo[2.2.1]hept-2-yl]oxy}carbonyl)oxy]androsta-1,4-diene-17-carboxylic acid

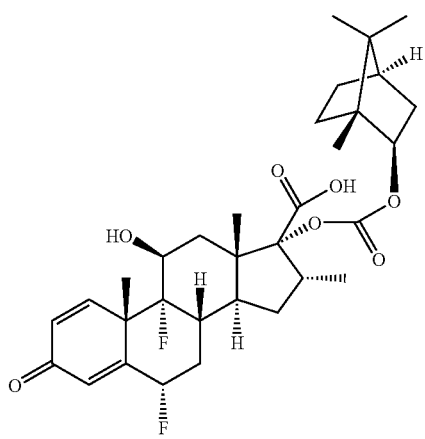

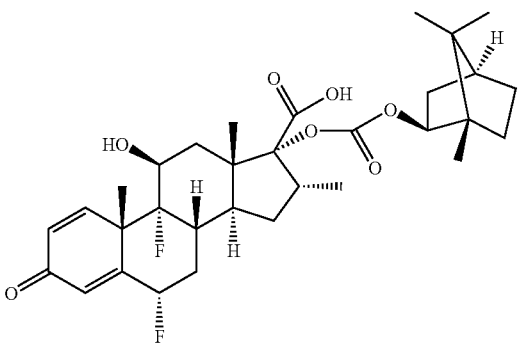

A solution of (+/−) isoborneol (154 mg, 1 mmol) and pyridine (81 μl, 1 mmol) in anhydrous dichloromethane (2 ml) was added portionwise over 10 min to a stirred and cooled (ice) solution of triphosgene (98 mg, 0.33 mmol) in anhydrous dichloromethane (4 ml) under nitrogen. After 1 h, approximately half of the resulting chloroformate solution was added to a solution of (6α,11β,16α,17α)-6,9-difluoro-11,17-dihydroxy-16-methyl-3-oxoandrosta-1,4-diene-17-carboxylic acid (200 mg, 0.5 mmol) in pyridine (2 ml) and the mixture stirred at room temperature overnight. The remainder of the chloroformate solution was then added and after 2 hours the solvent was evaporated in vacuo and the remaining residue stirred with 2M hydrochloric acid. The resulting precipitate was collected by filtration and dried in vacuo to give the title compound as a white solid (341 mg): LCMS retention time 3.85 min.

31

Intermediate 23: (6α,11β,16α,17α)-6,9-Difluoro-11-hydroxy-16-methyl-3-oxo-17-{[(1,2,2-trimethylpropyl)oxy]carbonyl}oxy)androsta-1,4-diene-17-carboxylic acid

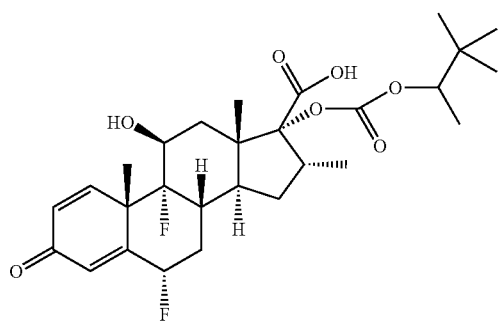

Prepared from 3,3-dimethyl-2-butanol using a method similar to that described for (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.44 and 3.54 min.

Intermediate 24: (6α,11β,16α,17α)-6,9-Difluoro-11-hydroxy-16-methyl-17-[({[1-(1-methylethyl)butyl]oxy}carbonyl)oxy]-3-oxoandrosta-1,4-diene-17-carboxylic acid

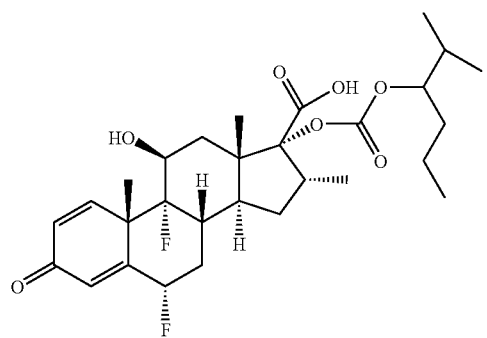

Prepared from 2-methyl-3-hexanol using a method similar to that described for (6α,11β,16α,17c)-17-({[(1-ethylpropyl)oxy]carbonyl}oxy)-6,9-difluoro-11-hydroxy-16-methyl-3-oxoandrosta-1,4-diene-17-carboxylic acid (Intermediate 3). LCMS retention time 3.66 min.

32

EXAMPLES

Example 1

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate

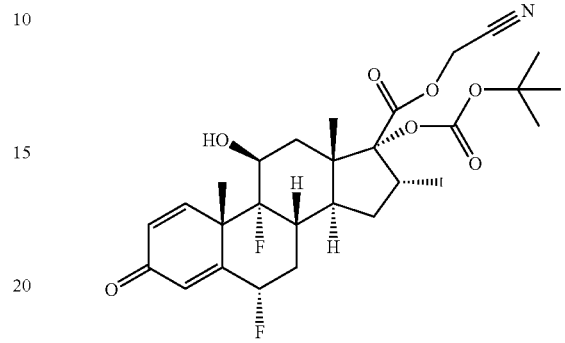

Sodium carbonate (321 mg, 3 mmol) was added to a solution of (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylic acid (Intermediate 1) (150 mg, 0.3 mmol) in N,N-dimethylformamide (3 ml) under nitrogen and the mixture stirred at room temperature for 15 min and then cooled in ice. Bromoacetonitrile (55 μl, 0.815 mmol) was added and the mixture allowed to warm to room temperature and stirred overnight. Diethylamine (40 μl, 0.51 mmol) was added and the mixture was then added dropwise to 2M hydrochloric acid (20 ml). The product was extracted into ethyl acetate and the extract was dried and evaporated and purified on a Bond Elut cartridge using a 0-100% cyclohexane/ether gradient to give the title compound (123 mg): LCMS retention time 3.51 min, m/z 536 MH$^+$

Example 2

Cyanomethyl (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylate

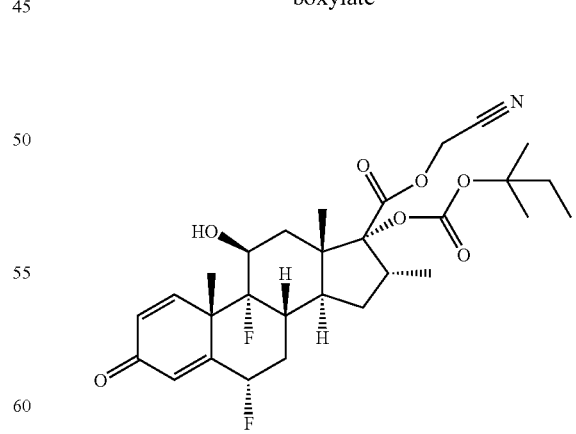

Example 2 was prepared from (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylic acid (Intermediate 2) using a method similar to that described for Example 1. LCMS retention time 3.59 min, m/z 550 MH$^+$

Example 3

Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate

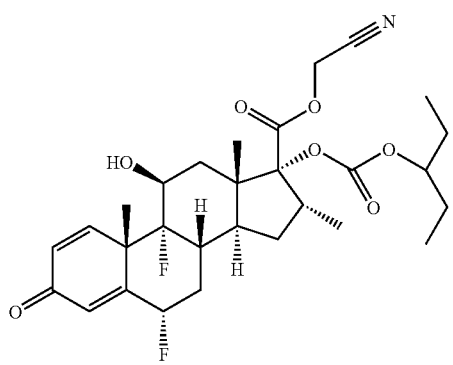

Example 3 was prepared from 6α,11β,16α,17α)-17-({[(1-ethylpropyl)oxy]carbonyl}oxy)-6,9-difluoro-11-hydroxy-16-methyl-3-oxoandrosta-1,4-diene-17-carboxylic acid (Intermediate 3) using a method similar to that described for Example 1. LCMS retention time 3.61 min, m/z 550 MH+

Example 4

Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate

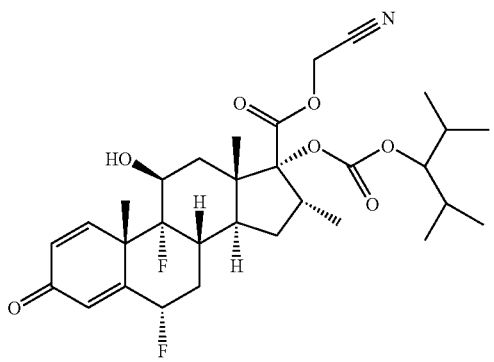

Example 4 was prepared from 6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylic acid (Intermediate 4) using a method similar to that described for Example 1. LCMS retention time 3.77 min, m/z 578 MH+

Example 5

Cyanomethyl (6α,11β,16α,17α)-17-({[(2-ethylbutyl)oxy]carbonyl}oxy)-6,9-difluoro-11-hydroxy-16-methyl-3-oxoandrosta-1,4-diene-17-carboxylate

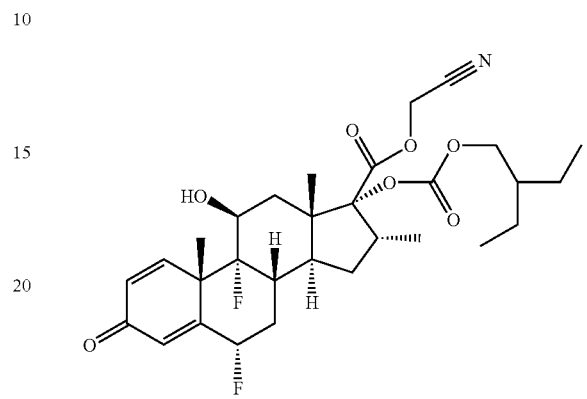

Example 5 was prepared from (6α,11β,16α,17α)-17-({[(2-ethylbutyl)oxy]carbonyl}oxy)-6,9-difluoro-11-hydroxy-16-methyl-3-oxoandrosta-1,4-diene-17-carboxylic acid) (Intermediate 5) using a method similar to that described for Example 1. LCMS retention time 3.67 min, m/z 564 MH+

Example 6

Cyanomethyl (6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylate

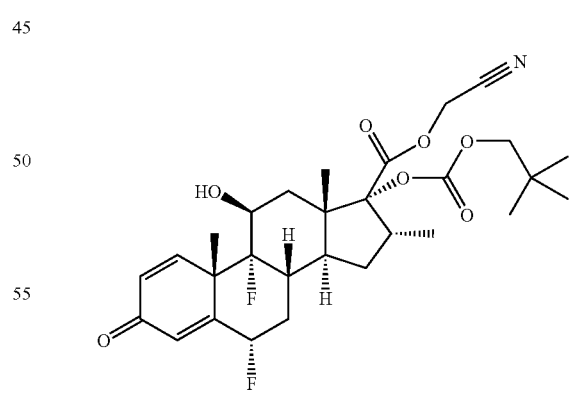

Example 6 was prepared from (6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylic acid (Intermediate 6) using a method similar to that described for Example 1. LCMS retention time 3.56 min, m/z 550 MH+

Example 7

Cyanomethyl (6α,11β,16α,17α)-17-({[(1-ethyl-2-methylpropyl)oxy]carbonyl}oxy)-6,9-difluoro-11-hydroxy-16-methyl-3-oxoandrosta-1,4-diene-17-carboxylate

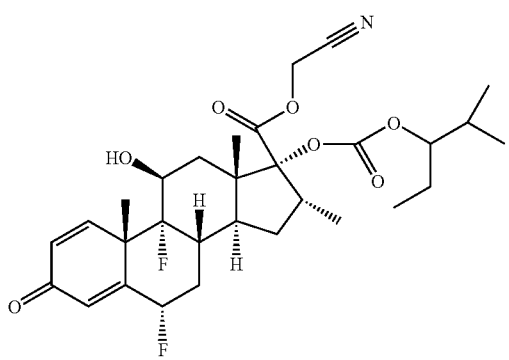

Example 7 was prepared as a mixture of diastereomers from (6α,11β,16α,17α)-17-({[(1-ethyl-2-methylpropyl)oxy]carbonyl}oxy)-6,9-difluoro-11-hydroxy-16-methyl-3-oxoandrosta-1,4-diene-17-carboxylic acid (Intermediate 7) using a method similar to that described for Example 1. LCMS retention time 3.69 min, m/z 564 MH+

Example 8

Cyanomethyl (6α,11β,16α,17α)-17-({[(1,2-dimethylpropyl)oxy]carbonyl}oxy)-6,9-difluoro-11-hydroxy-16-methyl-3-oxoandrosta-1,4-diene-17-carboxylate

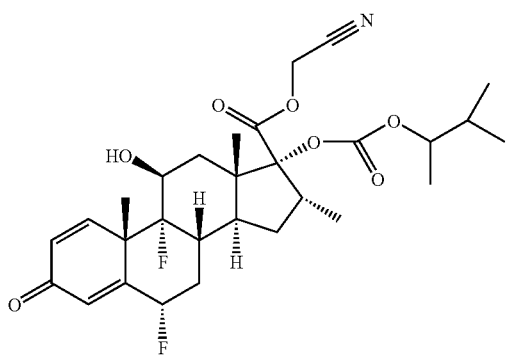

Example 8 was prepared as a mixture of diastereomers from (6α,11β,16α,17α)-17-({[(1,2-dimethylpropyl)oxy]carbonyl}oxy)-6,9-difluoro-11-hydroxy-16-methyl-3-oxoandrosta-1,4-diene-17-carboxylic acid (Intermediate 8) using a method similar to that described for Example 1. LCMS retention time 3.62 min, m/z 550 MH+

Example 9

Cyanomethyl (6α,11β,16α,17α)-17-{[(cyclopentyloxy)carbonyl]oxy}-6,9-difluoro-11-hydroxy-16-methyl-3-oxoandrosta-1,4-diene-17-carboxylate

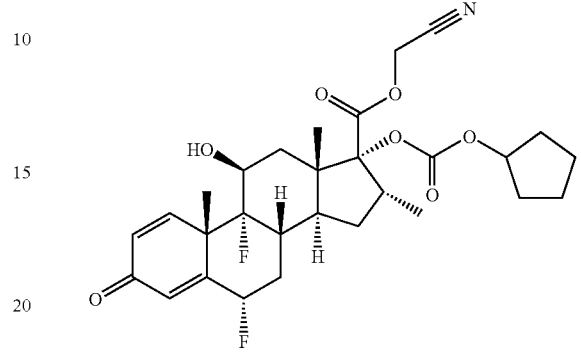

Example 9 was prepared from (6α,11β,16α,17α)-17-{[(cyclopentyloxy)carbonyl]oxy}-6,9-difluoro-11-hydroxy-16-methyl-3-oxoandrosta-1,4-diene-17-carboxylic acid (Intermediate 9) using a method similar to that described for Example 1: LCMS retention time 3.69 min, m/z 548 MH+

Example 10

Cyanomethyl (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylate

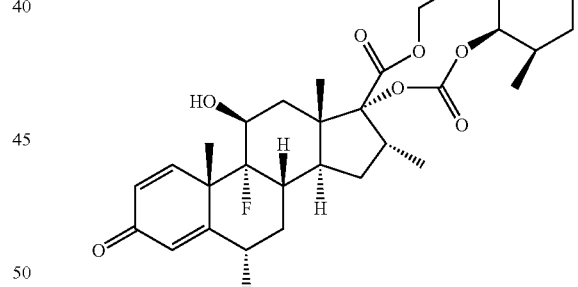

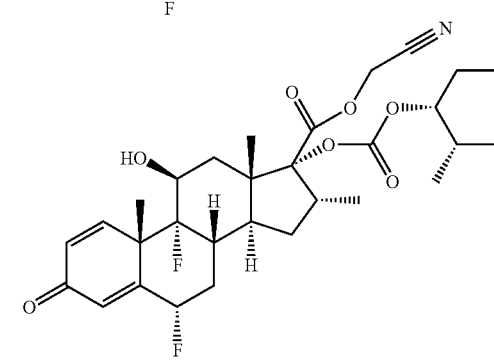

Example 10 was prepared as a mixture of diastereomers from (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylic acid (Intermediate 10) using a method similar to that described for Example 1. LCMS retention time 3.67 min, m/z 576 MH+

Example 11

Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate

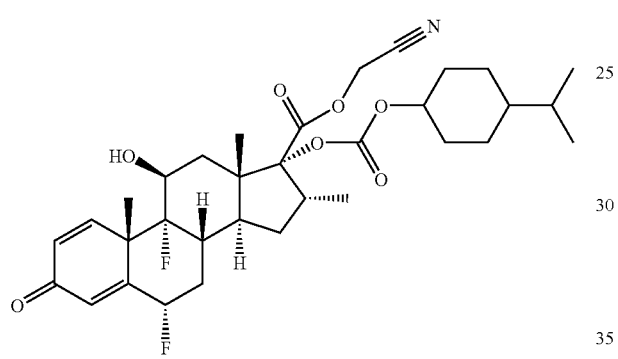

Example 11 was obtained as a ca 3:1 mixture of diastereoisomers from 6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylic acid) (Intermediate 11) using a method similar to that described for Example 1. The diastereomers were then separated by mass directed preparative HPLC to give the Minor Isomer Example 11A LCMS retention time 3.88 min, m/z 604 MH+. 1H-NMR: (DMSO-d6, 400 MHz) 17α cyclohexyl CH proton (adjacent to the carbonate) δ 4.67 (m, 1H).

Major Isomer Example 11B

LCMS retention time 3.94 min, m/z 604 MH+. 1H-NMR: (DMSO-d6, 400 MHz) 17a cyclohexyl CH proton (adjacent to the carbonate) δ 4.33 (m, 1H).

Example 12

Cyanomethyl (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate

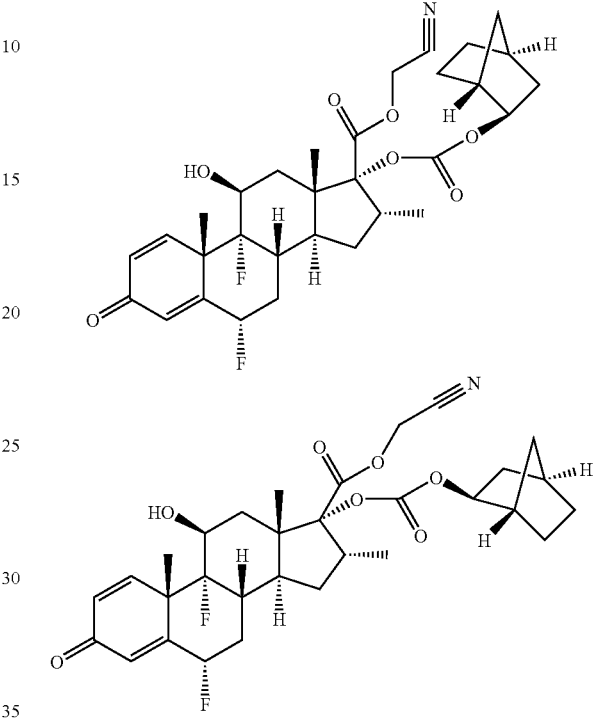

Example 12 was prepared as a mixture of diastereomers from (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylic acid (Intermediate 12) using a method similar to that described for Example 1. LCMS retention time 3.62 min, m/z 574 MH+

Example 13

Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate

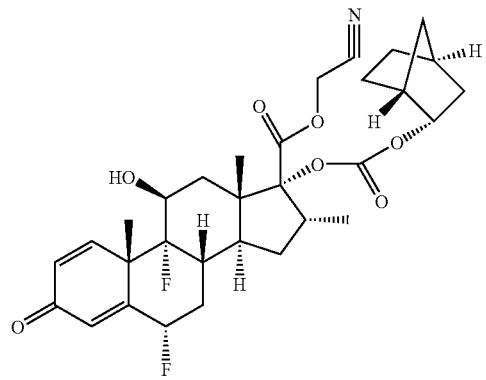

-continued

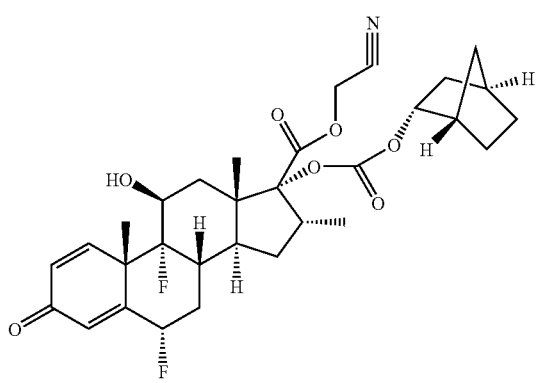

Example 13 was prepared as a mixture of diastereomers from (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylic acid) (intermediate 13) using a method similar to that described for Example 1. LCMS retention time 3.61 min, m/z 574 MH+

Example 14

Cyanomethyl (6α,11β,16α,17α)-6,9-difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylate

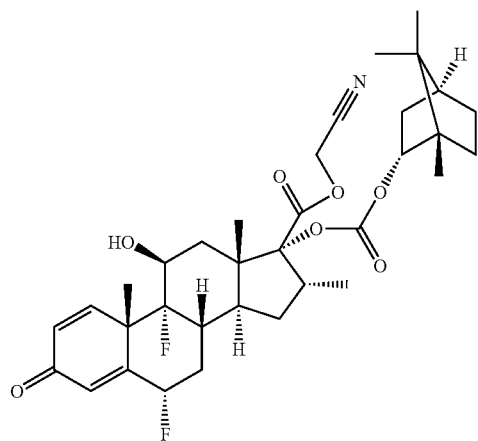

Example 14 was prepared from (6α,11β,16α,17α)-6,9-difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylic acid (Intermediate 14) using a method similar to that described for Example 1. The crude product was purified on a 5 g silica Bond Elut cartridge eluting with 0-100% ethyl acetate in cyclohexane gradient over 40 mins to give the title compound: LCMS retention time 3.92 min, m/z 616 MH+

Example 15

Cyanomethyl (6α,11β,16α,17α)-6,9-difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylate

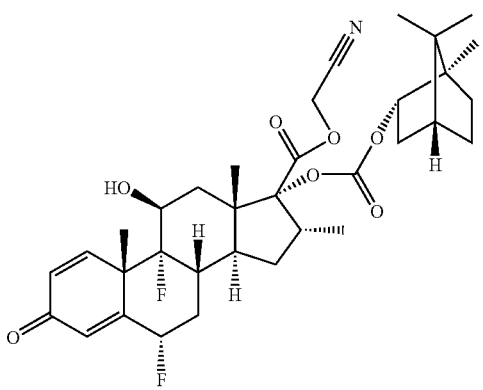

Example 15 was prepared from (6α,11β,16α,17α)-6,9-difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylic acid (Intermediate 15) using a method similar to that described for Example 1. The crude product was purified on a 5 g silica Bond Elut cartridge eluting with 0-100% ethyl acetate in cyclohexane gradient over 40 mins to give the title compound: LCMS retention time 3.92 min, m/z 616 MH+

Example 16

Cyanomethyl (6α,11β,16α,17α)-6,9-difluoro-11-hydroxy-16-methyl-3-oxo-17-[({[(1R,2R,3R,5S)-2,6,6-trimethylbicyclo[3.1.1]hept-3-yl]oxy}carbonyl)oxy]androsta-1,4-diene-17-carboxylate

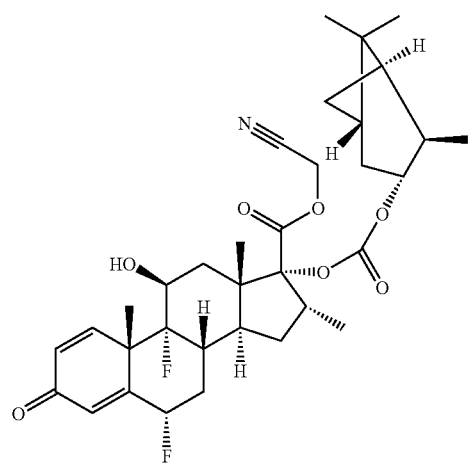

Example 16 was prepared from (6α,11β,16α,17α)-6,9-difluoro-11-hydroxy-16-methyl-3-oxo-17-[({[(1R,2R,3R,5S)-2,6,6-trimethylbicyclo[3.1.1]hept-3-yl]oxy}carbonyl)oxy]androsta-1,4-diene-17-carboxylic acid (Intermediate 16) using a method similar to that described for Example 1.

The crude product was purified on a 5 g silica Bond Elut cartridge eluting with 0-100% ethyl acetate in cyclohexane gradient over 40 mins to give the title compound: LCMS retention time 3.97 min, m/z 616 MH$^+$ Example 17

Cyanomethyl (6α,11β,16α,17α)-6,9-difluoro-11-hydroxy-16-methyl-3-oxo-17-[({[(1S,2S,3S,5R)-2,6,6-trimethylbicyclo[3.1.1]hept-3-yl]oxy}carbonyl)oxy]androsta-1,4-diene-17-carboxylate

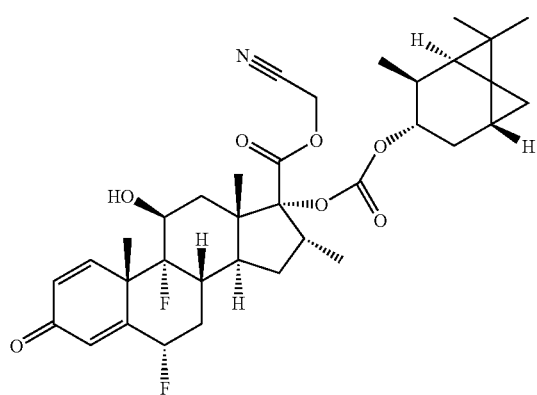

Example 17 was prepared from (6α,11β,16α,17α)-6,9-difluoro-11-hydroxy-16-methyl-3-oxo-17-[({[(1S,2S,3S,5R)-2,6,6-trimethylbicyclo[3.1.1]hept-3-yl]oxy}carbonyl)oxy]androsta-1,4-diene-17-carboxylic acid (Intermediate 17) using a method similar to that described for Example 1. The crude product was purified on a 5 g silica Bond Elut cartridge eluting with 0-100% ethyl acetate in cyclohexane gradient over 40mins to give the title compound: LCMS retention time 3.97 min, m/z 616 MH$^+$ Example 18

Cyanomethyl (6α,11β,16α,17α)-6,9-difluoro-11-hydroxy-16-methyl-3-oxo-17-[({[(1R,2R,4S)-1,3,3-trimethylbicyclo[2.2.1]hept-2-yl]oxy}carbonyl)oxy]androsta-1,4-diene-17-carboxylate

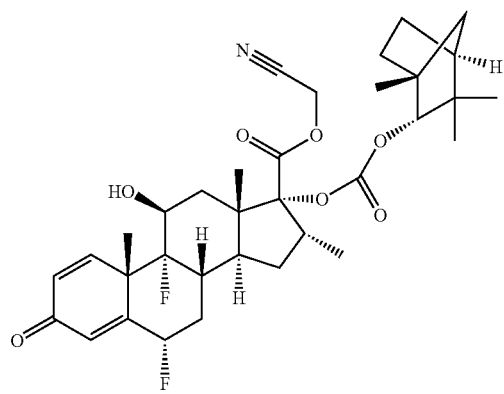

Example 18 was prepared from (6α,11β,16α,17α)-6,9-difluoro-11-hydroxy-16-methyl-3-oxo-17-[({[(1R,2R,4S)-1,3,3-trimethylbicyclo[2.2.1]hept-2-yl]oxy}carbonyl)oxy]androsta-1,4-diene-17-carboxylic acid (Intermediate 18) using a method similar to that described for Example 1. The crude product was purified on a 5 g silica Bond Elut cartridge eluting with 0-100% ethyl acetate in cyclohexane gradient over 40mins to give the title compound: LCMS retention time 3.97 min, m/z 616 MH$^+$ Example 19

Cyanomethyl (6α,11β,16α,17α)-17-({[(trans-4-ethylcyclohexyl)oxy]carbonyl}oxy)-6,9-difluoro-11-hydroxy-16-methyl-3-oxoandrosta-1,4-diene-17-carboxylate

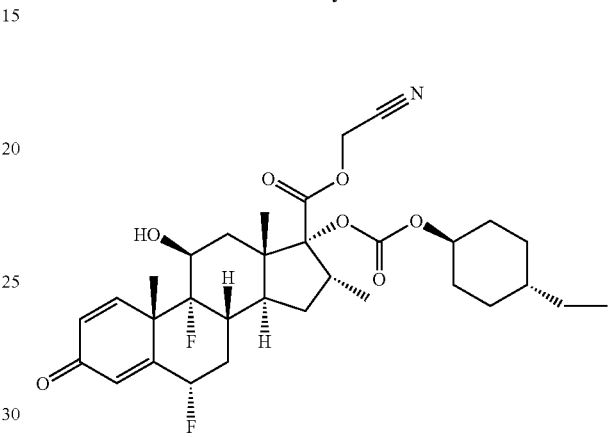

Example 19 was prepared from (6α,11β,16α,17α)-17-({[(trans-4-ethylcyclohexyl)oxy]carbonyl}oxy)-6,9-difluoro-11-hydroxy-16-methyl-3-oxoandrosta-1,4-diene-17-carboxylic acid (Intermediate 19) using a method similar to that described for Example 1. The crude product was purified on a 5 g silica Bond Elut cartridge eluting with 0-100% diethylether in cyclohexane gradient over 40mins to give the title compound: LCMS retention time 3.90 min, m/z 590 MH$^+$ Example 20

Cyanomethyl (6α,11β,16α,17α)-17-({[(cis-4-ethylcyclohexyl)oxy]carbonyl}oxy)-6,9-difluoro-11-hydroxy-16-methyl-3-oxoandrosta-1,4-diene-17-carboxylate

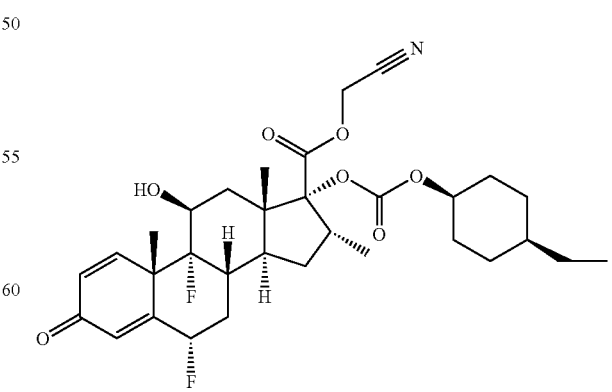

Example 20 was prepared from (6α,11β,16α,17α)-17-({[(cis-4-ethylcyclohexyl)oxy]carbonyl}oxy)-6,9-difluoro- 11-hydroxy-16-methyl-3-oxoandrosta-1,4-diene-17-carboxylic acid (Intermediate 20) using a method similar to that described for Example 1. The crude product was purified on a 5 g silica Bond Elut cartridge eluting with 0-100% diethyl-ether in cyclohexane gradient over 20mins to give the title compound: LCMS retention time 3.86 min, m/z 590 MH+

Example 21

Cyanomethyl (6α,11β16α,17α)-6,9-difluoro-11-hydroxy-16-methyl-3-oxo-17-({[(1-propylbutyl)oxy]carbonyl}oxy)androsta-1,4-diene-17-carboxylate

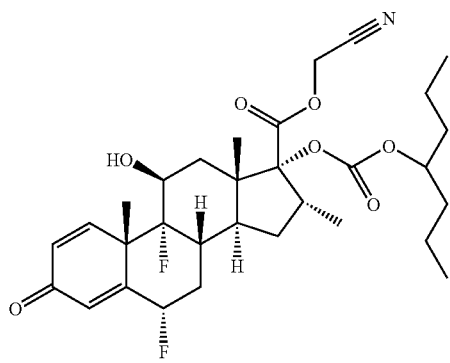

Example 21 was prepared from (6α,11β,16α,17α)-6,9-difluoro-11-hydroxy-16-methyl-3-oxo-17-({[(1-propylbutyl)oxy]carbonyl}oxy)androsta-1,4-diene-17-carboxylic acid (Intermediate 21) using a method similar to that described for Example 1. The crude product was purified on a 5 g silica Bond Elut cartridge eluting with 0-100% diethyl-ether in cyclohexane gradient over 20mins to give the title compound: LCMS retention time 3.82 min, m/z 578 MH+

Example 22

Cyanomethyl (6α,11β,16α,17α)-6,9-difluoro-11-hydroxy-16-methyl-3-oxo-17-[({[(1RS,2RS,4RS)-1,7,7-trimethylbicyclo[2.2.1]hept-2-yl]oxy}carbonyl)oxy]androsta-1,4-diene-17-carboxylate

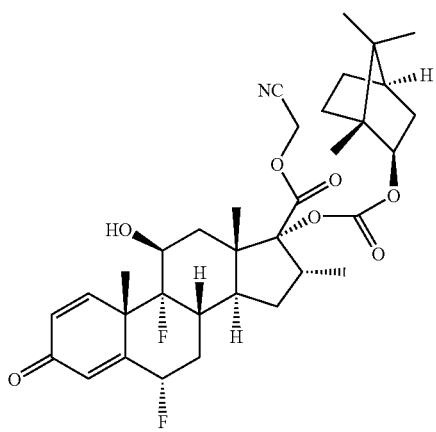

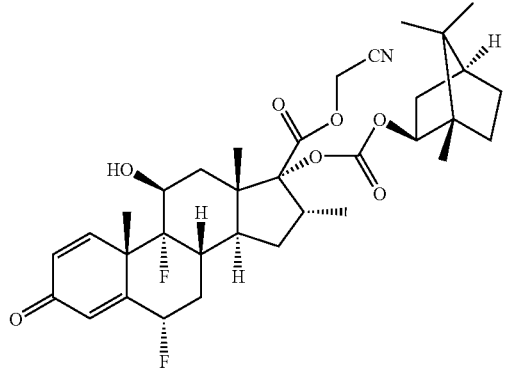

Example 22 was prepared as a mixture of diastereomers from (6α,11β,16α,17α)-6,9-difluoro-11-hydroxy-16-methyl-3-oxo-17-[({[(1RS,2RS,4RS)-1,7,7-trimethylbicyclo[2.2.1]hept-2-yl]oxy}carbonyl)oxy]androsta-1,4-diene-17-carboxylic acid (Intermediate 22) using a method similar to that described for Example 1. The crude product was purified on a 5 g silica Bond Elut cartridge eluted using 0-100% ethyl acetate in cyclohexane gradient over 40 minutes to give the title compound:

The diastereomers were then separated using normal phase HPLC to give:

Example 22A

LCMS retention time 3.93 min, m/z 616 MH+. 1H-NMR: (DMSO-$d_6$, 400 MHz) 17β cyanomethylene protons δ 5.03 (d, 16 Hz) and δ 5.00 (d, 16 Hz)

Example 22B

LCMS retention time 3.93 min, m/z 616 MH+. 1H-NMR: (DMSO-$d_6$, 400 MHz) 17β cyanomethylene protons δ 5.07 (d, 16 Hz) and δ 5.01 (d, 16 Hz)

Example 23

Cyanomethyl (6α,11β,16α,17α)-6,9-difluoro-11-hydroxy-16-methyl-3-oxo-17-({[(1,2,2-trimethylpropyl)oxy]carbonyl}oxy)androsta-1,4-diene-17-carboxylate

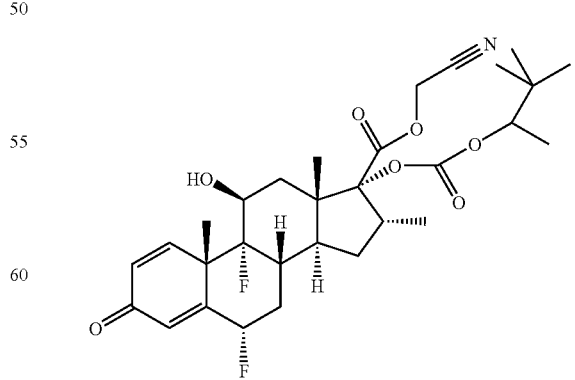

Example 23 was prepared as a crude mixture of diastereomers from (6α,11β,16α,17α)-6,9-difluoro-11-hydroxy-16- methyl-3-oxo-17-({[(1,2,2-trimethylpropyl)oxy]carbonyl}oxy)androsta-1,4-diene-17-carboxylic acid (Intermediate 23) using a method similar to that described for Example 1.

The crude diastereomers were then separated using normal phase HPLC to give:

Example 23A

LCMS retention time 3.88 min, m/z 564 MH$^+$. $^1$H-NMR: (DMSO-d$_6$, 400 MHz) 17β cyanomethylene protons δ 0 5.01 (s, 2H)

Example 23B

LCMS retention time 3.85 min, m/z 564 MH$^+$. $^1$H-NMR: (DMSO-d$_6$, 400 MHz) 17β cyanomethylene protons δ 5.10 (d, 16 Hz, 1H) and δ 5.01 (d, 16 Hz, 1H).

Example 24

Cyanomethyl (6α,11β,16α,17α)-6,9-difluoro-11-hydroxy-16-methyl-17-[({[1-(1-methylethyl)butyl]oxy}carbonyl)oxy]-3-oxoandrosta-1,4-diene-17-carboxylate

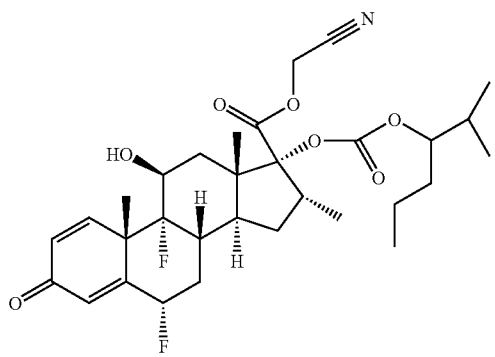

Example 24 was prepared as a mixture of diastereomers from (6α,11β,16α,17α)-6,9-difluoro-11-hydroxy-16-methyl-17-[({[1-(1-methylethyl)butyl]oxy}carbonyl)oxy]-3-oxoandrosta-1,4-diene-17-carboxylic acid (Intermediate 24) using a method similar to that described for Example 1. The crude product was purified on a 10 g silica Bond Elut cartridge eluting with 0-100% ethyl acetate in cyclohexane gradient over 40mins to give the title compound: LCMS retention time 3.79 min, m/z 578 MH$^+$ Pharmacological Activity Pharmacological activity may be assessed in functional in vitro assays of glucocorticoid agonist activity.

Assay for Transrepression Activity of the Glucocorticoid Agonists

The functional assay based on that described by K. P. Ray et al., Biochem J. (1997), 328, 707-715 provides a measure of transrepressive activity of a glucocorticoid agonist. A549 cells stably transfected with a reporter gene containing the NF-κB responsive elements from the ELAM gene promoter coupled to sPAP (secreted alkaline phosphatase) are treated with test compounds at appropriate doses for 1 hour at 37° C. The cells are then stimulated with tumour necrosis factor (TNF, 10 ng/ml) for 16 hours, at which time the amount of alkaline phosphatase produced is measured by a standard colourimetric assay. Dose response curves were constructed from which EC$_{50}$ values were estimated.

The pEC$_{50}$ values for compounds of Examples 1 to 24 were >7.5 in this assay.

The pEC$_{50}$ values for compounds of Examples 1 to 10, 11B, 12 and 13 were >9.5 in this assay.

The pEC$_{50}$ values of Examples 1, 2 and 13 were >10 in this assay.

Assay for Transactivation Activity of the Glucocorticoid Agonists

The functional assay based on that described by R. J. H. Austin et al., Eur Resp J. (2002), 20, 1386-1392 measures the ability of compounds to directly transactivate gene expression. A549 cells stably transfected with a reporter gene containing the glucocorticoid responsive region of the mouse mammary tumour virus long terminal repeat (MMTV-LTR) coupled to renilla luciferase were treated with test compounds at appropriate doses for 6 hour at 37° C. The amount of luciferase activity present within the cells is then determined by measuring the light emitted following incubation with a suitable substrate. Dose response curves were constructed from which EC$_{50}$ values were estimated and from which maximal responses are calculated relative to Dexamethasone (100%).

Compounds of Examples 1 to 24 showed maximal responses of <40% in this assay.

Compounds of Examples 1 to 4, 6, 10 to 18 and 20 to 23B showed maximal responses of <10% in this assay.

Assay for Progesterone Receptor Activity

A T225 flask of CV-1 cells at a density of 80% confluency was washed with PBS, detached from the flask using 0.25% trypsin and counted using a Sysmex KX-21N. Cells were diluted in DMEM containing 10% Hyclone, 2 mM L-Glutamate and 1% Pen/Strep at 140 cells/μl and transduced with 10% PRb-BacMam and 10% MMTV-BacMam. 70 ml of suspension cells were dispensed to each well of white Nunc 384-well plates, containing compounds at the required concentration. After 24 h 10 μl of Steady Glo were added to each well of the plates. Plates were incubated in the dark for 10 min before reading them on a Viewlux reader. Dose response curves were constructed from which pEC$_{50}$ values were estimated.

The pEC$_{50}$ values for compounds of Examples 1, 2, 5 to 13, 15 to 18 and 22A to 24 were <7 in this assay.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The patents and patent applications described in this application are herein incorporated by reference.

What is claimed is:

1. A compound of formula (I):

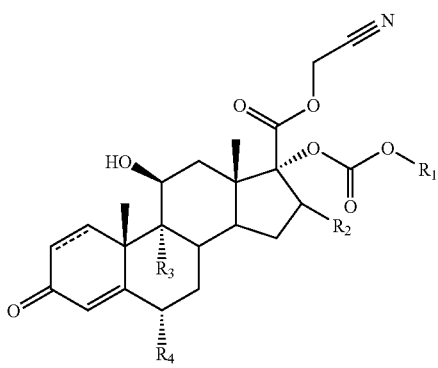

wherein
- $R_1$ represents $C_4$-$C_7$ branched alkyl group, a bicycloalkyl group, or a $C_5$-$C_6$ cycloalkyl which optionally may be substituted with a $C_1$-$C_4$ alkyl group;
- $R_2$ represents hydrogen, a methyl group, which may be in either the α or β configuration, or a methylene group;
- $R_3$ and $R_4$ are the same or a different group and each independently represents hydrogen, halogen or a methyl group;
- and ═ represents a single or a double bond.

2. A compound as claimed in claim 1 wherein $R_1$ represents $C_4$-$C_7$ branched alkyl group which is a 1,1-dimethylethyl, 1-ethylpropyl, 1,1-dimethylpropyl, 2,2-dimethylpropyl, 1,2-dimethylpropyl, 1-ethyl-2-methylpropyl, 2-methyl-1-(1-methylethyl)propyl, 2-ethylbutyl, 1-propylbutyl or a 1-(1-methylethyl)butyl group.

3. A compound as claimed in claim 1 wherein $R_1$ represents a $C_5$-$C_6$ cycloalkyl group optionally substituted with a $C_1$-$C_3$ alkyl group.

4. A compound as claimed in claim 3 wherein $R_1$ represents an optionally substituted $C_5$-$C_6$ cycloalkyl group which is a cyclopentyl, (1SR,2RS)-2-methylcyclohexyl, 4-(1-methylethyl)cyclohexyl, trans-4-ethylcyclohexyl or a cis-4-ethylcyclohexyl group.

5. A compound as claimed in claim 1 wherein $R_1$ represents a bicycloalkyl group which is a (1RS,2RS,4SR)-bicyclo[2.2.1]hept-2-yl, (1RS,2SR,4SR)-bicyclo[2.2.1]hept-2-yl, (1S,2R,4S)-1,7,7-trimethylbicyclo[2.2.1]hept-2-yl or a (1R,2S,4R)-1,7,7-trimethylbicyclo[2.2.1]hept-2-yl group.

6. A compound as claimed in claim 1 wherein $R_1$ represents a 1,1-dimethylethyl, 1,1-dimethylpropyl, 1-ethylpropyl, 2-methyl-1-(1-methylethyl)propyl, 2,2-dimethylpropyl, (1SR,2RS)-2-methylcyclohexyl, 4-(1-methylethyl)cyclohexyl Isomer B or a (1RS,2RS,4SR)-bicyclo[2.2.1]hept-2-yl or a (1RS,2SR,4SR)-bicyclo[2.2.1]hept-2-yl group.

7. A compound as claimed in claim 1 wherein $R_1$ represents a 1,1-dimethylpropyl group.

8. A compound as claimed in claim 1 wherein $R_1$ represents a 1,1-dimethylethyl group.

9. A compound as claimed in claim 1 wherein $R_2$ represents a methyl group in the α-configuration.

10. A compound as claimed in claim 1 wherein $R_3$ and $R_4$ are both fluorine.

11. A compound as claimed in claim 1 wherein ═ represents a double bond.

12. A compound which is:
Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate;
Cyanomethyl (6α,11β,16α,17α)-17-({[(1,1-dimethylpropyl)oxy]carbonyl}oxy)-6,9-difluoro -11-hydroxy-16-methyl-3-oxoandrosta-1,4-diene-17-carboxylate;
Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate;
Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate;
Cyanomethyl (6α,11β,16α,17α)-17-({[(2-ethylbutyl)oxy]carbonyl}oxy)-6,9-difluoro-11-hydroxy-16-methyl-3-oxoandrosta-1,4-diene-17-carboxylate;
Cyanomethyl (6α,11β,16α,17α)-17-({[(2,2-dimethylpropyl)oxy]carbonyl}oxy)-6,9-difluoro -11-hydroxy-16-methyl-3-oxoandrosta-1,4-diene-17-carboxylate;
Cyanomethyl (6α,11β,16α,17α)-17-({[(1-ethyl-2-methylpropyl)oxy]carbonyl}oxy)-6,9-difluoro-11-hydroxy-16-methyl-3-oxoandrosta-1,4-diene-17-carboxylate;
Cyanomethyl (6α,11β,16α,17α)-17-({[(1,2-dimethylpropyl)oxy]carbonyl}oxy)-6,9-difluoro -11-hydroxy-16-methyl-3-oxoandrosta-1,4-diene-17-carboxylate;
Cyanomethyl (6α,11β,16α,17α)-17-{[(cyclopentyloxy)carbonyl]oxy}-6,9-difluoro-11-hydroxy-16-methyl-3-oxoandrosta-1,4-diene-17-carboxylate;
Cyanomethyl (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylate;
Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate;
Cyanomethyl (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate;
Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate;
Cyanomethyl (6α,11β,16α,17α)-6,9-difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylate;
Cyanomethyl (6α,11β,16α,17α)-6,9-difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylate;
Cyanomethyl (6α,11β,16α,17α)-6,9-difluoro-11-hydroxy-16-methyl-3-oxo-17-[({[(1R,2R,3R,5S)-2,6,6-trimethylbicyclo[3.1.1]hept-3-yl]oxy}carbonyl)oxy]androsta-1,4-diene-17-carboxylate;
Cyanomethyl (6α,11β,16α,17α)-6,9-difluoro-11-hydroxy-16-methyl-3-oxo-17-[({[(1S,2S,3S,5R)-2,6,6-trimethylbicyclo[3.1.1]hept-3-yl]oxy}carbonyl)oxy]androsta-1,4-diene-17-carboxylate;
Cyanomethyl (6α,11β,16α,17α)-6,9-difluoro-11-hydroxy-16-methyl-3-oxo-17-[({[(1R,2R,4S)-1,3,3-trimethylbicyclo[2.2.1]hept-2-yl]oxy}carbonyl)oxy]androsta-1,4-diene-17-carboxylate;

Cyanomethyl (6α,11β,16α,17α)-17-({[(trans-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(cis-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-3-oxo-17-({[(1-propylbutyl)oxy]carbonyl}oxy)androsta-1,4-diene-17-carboxylate;

Cyanomethyl (6α,11β,16α,17α)-6,9-difluoro-11-hydroxy-16-methyl-3-oxo-17-[({[(1R,2R,4R)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-[({[(1S,2S,4S)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-({[(1,2,2-trimethylpropyl)oxy]carbonyl}oxy)androsta-1,4-diene-17-carboxylate; or Cyanomethyl (6α,11β,16α,17α)-6,9-difluoro-11-hydroxy-16-methyl-17-[({[1-(1-methylethyl)butyl]oxy}carbonyl)oxy]-3-oxoandrosta-1,4-diene-17-carboxylate.

13. A compound as claimed in claim 12 which is:

Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate;

Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate;

Cyanomethyl (6α,11β,16α,17α)-17-({[(2-ethylbutyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[(1SR,2RS)-2-methylethylcyclohexyl]oxy}carbonyl)oxy]-3-oxoandrosta-1,4-diene-17-carboxylate;

Cyanomethyl (6α,11β,16α,17α)-17-({[(2,2-dimethylpropyl)oxy]carbonyl}oxy)-6,9-difluoro -11-hydroxy-16-methyl-3-oxoandrosta-1,4-diene-17-carboxylate;

Cyanomethyl (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylpropyl)oxy]carbonyl}oxy)-6,9-difluoro -11-hydroxy-16-methyl-3-oxoandrosta-1,4-diene-17-carboxylate;

Cyanomethyl (6α,11β,16α,17α)-17-({[(1-ethyl-2-methylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(2,2-dimethylpropyl)oxy]carbonyl}oxy)-6,9-difluoro -11-hydroxy-16-methyl-3-oxoandrosta-1,4-diene-17-carboxylate;

Cyanomethyl (6α,11β,16α,17α)-17-{[(cyclopentyloxy)carbonyl]oxy}-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-3-oxo-17-[({[(1S,2R,4S)-1,7,7-trimethylbicyclo[2.2.1]hept-2-yl]oxy}carbonyl)oxy]androsta-1,4-diene-17-carboxylate;

Cyanomethyl (6α,11β,16α,17α)-6,9-difluoro-11-hydroxy-16-methyl-3-oxo-17-[({[(1R,2S,4R)-1,7,7-trimethylbicyclo[2.2.1]hept-2-yl]oxy}carbonyl)oxy]androsta-1,4-diene-17-carboxylate;

Cyanomethyl (6α,11β,16α,17α)-17-({[(trans-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(cis-4-ethylcyclohexyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-3-oxo-17-({[(1-propylbutyl)oxy]carbonyl}oxy)androsta-1,4-diene-17-carboxylate; or Cyanomethyl (6α,11β,16α,17α)-6,9-difluoro-11-hydroxy-16-methyl-17-[({[1-(1-methylethyl)butyl]oxy}carbonyl)oxy]-3-oxoandrosta-1,4-diene-17-carboxylate.

14. A compound as claimed in claim 13 which is:

Cyanomethyl (6α,11β,16α,17α)-17-({[(1,1-dimethylpropyl)oxy]carbonyl}oxy)-6,9-difluoro -11-hydroxy-16-methyl-3-oxoandrosta-1,4-diene-17-carboxylate;

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1-ethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[2-methyl-1-(1-methylethyl)propyl]oxy}carbonyl)oxy]-3-oxoandrosta-1,4-diene-17-carboxylate;

Cyanomethyl (6α,11β,16α,17α)-17-({[(2,2-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-6,9-difluoro-11-hydroxy-16-methyl-17-[({[(1SR,2RS)-2-methylcyclohexyl]oxy}carbonyl)oxy]-3-oxoandrosta-1,4-diene-17-carboxylate;

Cyanomethyl (6α,11β,16α,17α)-6,9-difluoro-11-hydroxy-16-methyl-17-[({[4-(1-methylethyl)cyclohexyl]oxy}carbonyl)oxy]-3-oxoandrosta-1,4-diene-17-carboxylate;

Cyanomethyl (6α,11β,16α,17α)-17-({[(1RS,2RS,4SR)-bicyclo[2.2.1]hept-2-yloxy]carbonyl}oxy)-6,9-difluoro-11-hydroxy-16-methyl-3-oxoandrosta-1,4-diene-17-carboxylate; or Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate.

15. A compound as claimed in claim 12 which is:

Cyanomethyl (6α,11β,16α,17α)-17-({[(1,1-dimethylpropyl)oxy]carbonyl}oxy)-6,9-difluoro-11-hydroxy-16-methyl-3-oxoandrosta-1,4-diene-17-carboxylate;

Cyanomethyl (6α,11β,16α,17α)-17-({[(1,1-dimethylethyl)oxy]carbonyl}oxy)-6,9-difluoro-11-hydroxy-16-methyl-3-oxoandrosta-1,4-diene-17-carboxylate; or Cyanomethyl (6α,11β,16α,17α)-17-({[(1RS,2SR,4SR)-bicyclo[2.2.1]hept-2-yloxy]carbonyl}oxy)-6,9-difluoro-11-hydroxy-16-methyl-3-oxoandrosta-1,4-diene-17-carboxylate.

16. A pharmaceutical composition comprising a compound of formula (I) as defined in claim 1 in admixture with one or more physiologically acceptable diluents or carriers.

17. A pharmaceutical aerosol formulation comprising a compound of formula (I) as defined in claim 1, and a fluorocarbon or hydrogen-containing chlorofluoro carbon as propellant, optionally in combination with a surfactant and/or a cosolvent.

18. A pharmaceutical composition according to claim 17 which further comprises another therapeutically active agent.

19. A pharmaceutical composition according to claim 18 in which said another therapeutically active agent is a $\beta_2$-adrenoreceptor agonist.

20. A method for the treatment of a human or animal subject with an inflammatory and/or allergic condition, which method comprises administering to said human or animal subject an effective amount of a compound of formula (I) as defined in claim 1.

21. A process for preparing a compound of formula (I) which comprises reaction of a carboxylic acid of formula (II);

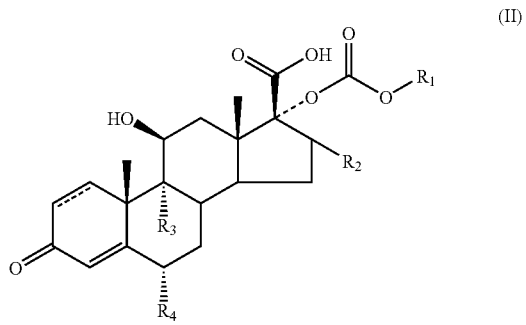

wherein $R_1$, $R_2$, $R_3$, $R_4$ and ==== are as defined in claim 1;
with a compound of formula L-CH$_2$—CN wherein L represents a leaving group.

* * * * *